(12) United States Patent
Bonnert et al.

(10) Patent No.: US 8,022,248 B2
(45) Date of Patent: Sep. 20, 2011

(54) SUBSTITUTED ACIDS FOR THE TREATMENT OF RESPIRATORY DISEASES

(75) Inventors: Roger Victor Bonnert, Leicestershire (GB); Stephen Thom, Leicestershire (GB); Anil Patel, Leicestershire (GB); Timothy Jon Luker, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 1001 days.

(21) Appl. No.: 11/571,707

(22) PCT Filed: Jul. 6, 2005

(86) PCT No.: PCT/GB2005/002650
§ 371 (c)(1),
(2), (4) Date: Jan. 5, 2007

(87) PCT Pub. No.: WO2006/005909
PCT Pub. Date: Jan. 19, 2006

(65) Prior Publication Data
US 2008/0114002 A1    May 15, 2008

(30) Foreign Application Priority Data
Jul. 8, 2004    (GB) .................................. 0415320.1

(51) Int. Cl.
C07C 317/14 (2006.01)
C07C 65/00 (2006.01)
(52) U.S. Cl. ........................................ 562/429; 562/465
(58) Field of Classification Search .................. None
See application file for complete search history.

(56) References Cited

U.S. PATENT DOCUMENTS

| | | | |
|---|---|---|---|
| 3,278,524 A | 10/1966 | Johnson et al. |
| 3,920,846 A | 11/1975 | Hanauye et al. |
| 3,985,779 A | 10/1976 | Tanaka et al. |
| 4,234,742 A | 11/1980 | Cognacq et al. |
| 4,248,618 A | 2/1981 | Serban et al. |
| 4,670,566 A | 6/1987 | Walsh et al. |
| 5,006,542 A | 4/1991 | Hall et al. |
| 5,145,790 A | 9/1992 | Mattingly et al. |
| 5,411,972 A | 5/1995 | Komoto et al. |
| 5,413,891 A | 5/1995 | Matsuura et al. |
| 5,532,371 A | 7/1996 | Komoto et al. |
| 5,703,099 A | 12/1997 | Hamanaka et al. |
| 6,150,413 A | 11/2000 | Bernardon et al. |
| 6,376,546 B1 | 4/2002 | Shoda et al. |
| 6,417,212 B1 | 7/2002 | Brooks et al. |
| 7,056,942 B2 | 6/2006 | Hildesheim et al. |
| 7,067,507 B2 | 6/2006 | Pullet et al. |
| 7,737,135 B2 | 6/2010 | Luker et al. |
| 2004/0029933 A1 | 2/2004 | Zhao et al. |
| 2004/0097555 A1 | 5/2004 | Ohkawa et al. |
| 2004/0220237 A1 | 11/2004 | Fu et al. |
| 2005/0239881 A1 | 10/2005 | Dunn et al. |
| 2006/0211765 A1 | 9/2006 | Pairaudeau et al. |
| 2006/0264435 A1 | 11/2006 | Bonnert et al. |
| 2006/0293352 A1 | 12/2006 | Bonnert et al. |
| 2007/0249686 A1 | 10/2007 | Bonnert et al. |
| 2008/0114002 A1 | 5/2008 | Bonnert et al. |
| 2008/0132480 A1 | 6/2008 | Luker et al. |
| 2008/0255150 A1 | 10/2008 | Luker |
| 2008/0293775 A1 | 11/2008 | Bonnert et al. |
| 2009/0012151 A1 | 1/2009 | Bonnert et al. |
| 2009/0036535 A1 | 2/2009 | Luker et al. |
| 2009/0149448 A1 | 6/2009 | Alcaraz et al. |
| 2009/0192163 A1 | 7/2009 | Luker et al. |
| 2010/0160285 A1 | 6/2010 | Luker et al. |

FOREIGN PATENT DOCUMENTS

| | | |
|---|---|---|
| CH | 432119 | 9/1967 |
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |

(Continued)

OTHER PUBLICATIONS

Ueda et al, Chemical & Pharmaceutical Bulletin, Synthesis of 10-(4-methylpiperazino) dibenzo [b,f] thiepin and Related Compounds. Neurotropic and Psychotropic Agents, 1975, 23(10), pp. 2223-2231.*

Manske et al, Journal of the American Chemical Society, Synthesis and Reactions of Some Dibenzoxepins, 1950, 72, pp. 4797-4799.*

Atkinson et al, Journal of Medicinal Chemistry, Substituted (2-Phenoxyphenyl)acetic Acids with Antiinflammatory Activity. 1, 1983, 26, pp. 1353-1360.*

(Continued)

*Primary Examiner* — Paul A Zucker
(74) *Attorney, Agent, or Firm* — Fish & Richardson P.C.

(57) ABSTRACT

The invention relates to substituted acids of formula (I), where T, W, X, Y, Z, $R^1$ and $R^2$ as defined in the claims, as useful pharmaceutical compounds for treating asthma and rhinitis, pharmaceutical compositions containing them, and a processes for their preparation.

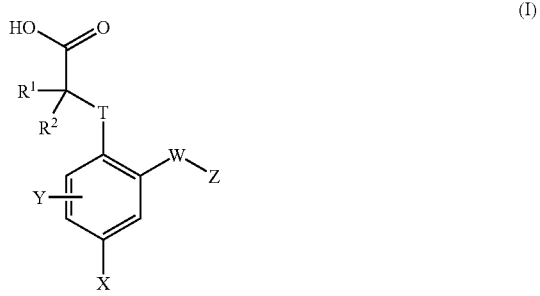

(I)

6 Claims, No Drawings

FOREIGN PATENT DOCUMENTS

| | | |
|---|---|---|
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.

Atkinson et al., "Substituted (2-Phenoxyphenyl)acetic Acids with Antiinflammatory Activity", *J. Med. Chem.*, vol. 26, 1983, pp. 1353-1360.

Baliah et al., "Fries rearrangement of the benzenesulphonates of xylenols", *Recueil des Travaux Chimiques des Pays-Bas*, vol. 80, 1961, pp. 139-148.

Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.

Brown et al., "Some Chlorinated Hydroxyphenoxyacetic Acids", *Journal of the Chemical Society*, 1955, pp. 3681-3687.

Budavari, S., "The merck Index, 13$^{th}$ edition", p. 3106, monograph 3108, XP-002347170, 2001.

Cavill et al., "The chemistry of plant-growth regulators. Part I. 2:4-dichloro-6-hydroxyphenoxyacetic acid and related compounds", *Journal of the Chemical Society*, 1954, pp. 565-569.

*Cecil Textbook of Medicine*, 20$^{th}$ ed. (1996), vol. 2, pp. 1992-1996.

*Cecil Textbook of Medicine*, 20$^{th}$ ed. (1996), vol. 2, pp. 2050-2057.

Clemo et al., "Strychnine and brucine. Part II", *Journal of the Chemical Society*, vol. 125, 1924, pp. 1751-1804, XP008053173.

Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.

FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.

Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.

Gaunt et al., "Metabolism of 4-chloro-2-methylphenoxyacetate by a soil pseudomonad", *Biochem. J.*, vol. 122, 1971, pp. 519-526.

Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", *J. Med. Chem.*, vol. 44, 2001, pp. 1758-1776.

Huston et al., "Chloro derivatives of o- and p-benzyl phenols. II. Some monochloro, dichloro and trichloro derivatives of ortho and para benzyl phenols", *Journal of the American Chemical Society*, vol. 55, No. 11, 1933, pp. 4639-4643.

Inukai et al., "*ortho*-Disubstituted *F*-benzenes. III. Preparation of (*F*-benzo)heterocyclic compounds from *F*-benzoic acid and *F*-phenol, and the reactions of some intermediary *F*-benzoyl- and F-phenoxy compounds", *Bull. Chem. Soc. Jpn.*, vol. 54, No. 11, 1981, pp. 3447-3452.

Janczewski et al., "Effect of Molecular Structure on Optical Properties of Sulfoxide Systems. *o*-Phenoxyphenylsulfinylacetic Acid and some of Their Derivatives. Part II", *Polish Journal of Chemistry*, vol. 62, No. 1-3, 1964, pp. 91-105, XP008053171.

Kmonicek et al., "(Tert-Amino)-11-(4-Methylpiperazino)Dibenzo[b,f]Thiepins and their 10,11-Dihydro Derivatives; Synthesis and Neuroleptic Activity", *Collection Czechoslov. Chem. Commun.*, vol. 52, 1987, pp. 792-803, XP-002347166.

Lehmler et al., "Synthesis of hydroxylated PCB metabolites with the Suzuki-coupling", *Chemosphere*, vol. 45, 2001, pp. 1119-1127.

Litvak et al., "Synthesis and S$_N$Ar reactions of new dioxins and predioxins", *Chemosphere*, vol. 43, No. 4-7, 2001, pp. 493-495.

Lupus erythematosus [online], [retrieved Dec. 28, 2006]. Retrieved from the Internet, URL; http://en.wikipedia.org/wiki/Lupus_erythematosus>.

Maeda et al., "Studies on the Synthesis and Analgesic and Anti-inflammatory Activities of 2-Thiazolylamino- and 2-Thiazolyloxy-arylacetic Acid Derivatives", *Chem. Pharm. Bull.*, vol. 31, No. 10, 1983, pp. 3424-3445, XP-002347167.

Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).

Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.

Moser et al., "Synthesis and Quantitative Structure-Activity Relationships of Diclofenac Analogues", *J. Med. Chem.*, vol. 33, 1990, pp. 2358-2368, XP-001024801.

Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.

Ong et al., "Synthesis and Analgesic Activity of Some Spiro[dibenz[b,f]oxepin-10,4'-piperidine] Derivatives", *J. Med. Chem.*, vol. 22, No. 7,1979, pp. 834-839, XP-002347163.

Rajsner et al., "Fluorinated tricyclic Neuroleptics: Synthesis and Pharmacology of 8-Fluoro-4-(4-Methylpiperazino)-4,5-Dihydrothieno[2,3-b]-1-Benzothiepin", *Collection Czechoslov. Chem. Commun.*, vol. 44, 1979, pp. 2997-3007, XP-002347164.

Selvi et al., "Vilsmeier cyclization of 2-amino phenoxyacetic acid", *Synthetic Communications*, vol. 31, No. 14, 2001, pp. 2199-2202.

Sindelar et al., "Synthesis of 3-Chloro-5-(4-Methylpiperazino)-6,7-Dihydro-5H-Dibenzo[b,g]Thiocin, An Eight-Membered Ring Homologue of The Neuroleptic Agent Octoclothepin", *Collection Czechoslov. Chem. Commun.*, vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[b,f]Thiepin", *Collection Czechoslov. Chem. Commun.*, vol. 46, 1981, pp. 118-140, XP-002347168.

Sindler-Kulyk et al., "Synthesis of New 3-(Phenoxyphenyl)sydnones", *J. Hetercyclic Chem.*, vol. 29, No. 2, 1992, pp. 1013-1015, XP-002347161.

Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", *J. Med. Chem.*, vol. 29, 1986, pp. 852-855.

Thuillier, G., "Derives des acides 24 aryloxyacetiques a activite neurotrope", *Chimique Therapeutique*, vol. 1, No. 2, 1966, pp. 82-86.

Walsh et al., "Antiinflammatory Activity of N-(2-Benzoylphenyl)alanine Derivatives", *J. Med. Chem.*, vol. 27, 1984, pp. 1317-1321, XP-002347162.

Wheatley et al., "2-Benzylphenol Derivatives. III. Basic Ethers", *Journal of American Chemical Society*, vol. 71, No. 11, 1949, pp. 3795-3797.

Database CA [Online] Chemical Abstracts Service, Columbus, Ohio, US; XP002372494 retrieved from STN Database accession No. 1956:16264 abstract & Ott, Donald G. et al: "A carbon-14 tracer study of the alkaline rearrangement of chlorophenanthraquinones" *Journal of the American Chemical Society*, vol. 77, 2325-2329 CODEN:JACSAT; ISSN:0002-7863, 1955.

Database CAPLUS [Online] Chemical Abstracts Service, Columbus, Ohio, US; 1992, XP002372495 retrieved from STN Database accession No. 1992:255529 abstract & Ram, Bhagat et al: "Potential hypolipidemic agents part VI: synthesis and biological activity of some new 4-chloro/methyl-2-pyrazolylphenoxy alkanoates", *Indian Drugs*, vol. 29, No. 6, 1992, pp. 258-262.

Database WPI 1-3, 5, Section Ch, Week 200365 19, 20, Derwent Publications Ltd., London, GB, AN 2003-689635 XP-002301315, WO03068744A1, Ishihara Sangyo Kaisha, Ltd., Aug. 21, 2003.

STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.

STN International, File CAPLUS, CAPLUS accession 1-5, 10, No. 1979:186607, document No. 90:186607, Ciba-Geigy, "Phenoxyphenoxyalkanecardoxylic acid derivatives", DE, A1, 2832435, 19790208.

STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & *Journal of Organic Chemistry* (1970), 36(2), 305-308.

STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.

STN International, File CAPLUS, CAPLUS accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.

STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.

STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.

STN International, File CAPLUS, CAPLUS accession 1, 3, 5, 10, No. 1971:498288, document No. 75:98288, Botez et al., "Phenoxybutyric acid sulfamides. I. Sulfamide derivatives of the $\alpha$-phenoxy-, $\alpha$-cresoxy-, and $\alpha$-xylenoxybutyric acids", Buletinul Institutului Politehnic din Iasi (1970), 16(1-2), 161-172.

STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, 19850729.

Vippagunta et al., "Crystalline solids", *Advanced Drug Delivery Reviews* 48:3-26 (2001).

Inflammatory Bowel Disease [online] {retrieved on Apr. 7, 2008 from the internet} {URL:http://www.emedicinehealth.com/script/main/art.asp?articlekey=59121&pf=3&page=8}.

Rheumatoid arthritis [online] {retrieved on Apr. 7, 2008 from the internet} {URL:http://www.nlm.nih. gov/medlineplus/ency/article/000431.htm}.

Asthma [online] [retrieved on May 30, 2008] retrieved from the Internet URL:http://www.nlm.nih.gov/medlineplus/ency/article/000141.htm.

AstraZeneca AB: WO03066046 & WO03066047, "The use of indole-3-acetic acids as CRTH2 receptor antagonists", *Expert Opin. Ther. Patents* 14(1):125-128 (2004).

Chiu et al., "Derivation and Properties of Recombinant Fab Antibodies to Coplanar Polychlorinated Biphenyls", *J. Agric. Food Chem.* 48:2614-2624 (2000).

Dalal et al., "Synthetic insecticides. I. Synthesis of $\alpha$, $\alpha$-bis(aryl)-$\beta$, $\beta$, $\gamma$-trichlorobutanes", STN Accession No. 1950:35789, Document No. 44:35789, Abstract of Journal of the Indian Chemical Society 26:549-52 (1949).

Ebenezar et al., "Prostaglandins in the patent literature", *Expert Opin. Ther. Patents* 17(9):1131-1145 (2007).

Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).

Gavezzotti, "Are Crystal Structures Predictable?", *Acc. Chem. Res.* 27:309-314 (1994).

Golub et al., "Molecular Classification of Cancer: Class Discovery and Class Prediction by Gene Expression Monitoring", *Science* 286:531-537 (1999).

Hazlet et al., "Bromination of 2-phenylphenyl acetate", STN Accession No. 1941:37645, Document No. 35:37645, Abstract of Journal of the American Chemical Society 63:1890-2 (1941).

Ly et al., "Small-molecule CRTH2 antagonists for the treatment of allergic inflammation: an overview", *Expert Opin. Invest. Drugs* 14(7):769-773 (2005).

Morissette et al., "High-throughput crystallization: polymorphs, salts, co-crystals and solvates of pharmaceutical solids", *Advanced Drug Delivery Reviews* 56:275-300 (2004).

Ono Pharm. Co. Ltd: WO03022813 & WO03022814, "The use of prostaglandin $D_2$ receptor antagonists to treat allergic rhinitis", *Expert Opin. Ther. Patents* 13(10):1657-1661 (2003).

Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).

Ulven et al., "Targeting of the Prostaglandin $D_2$ Receptors DP and CRTH2 for Treatment of Inflammation", *Current Topics in Medicinal Chemistry* 6:1427-1444 (2006).

Wermuth, "Molecular Variations Based on Isosteric Replacements", The Practice of Medicinal Chemistry, 1996, chapter 13, pp. 203-237.

Rhinitis [online] [retrieved on Nov. 12, 2008 from the internet] URL:http://www.healthline.com/galecontent/rhinitis?print=true.

Preventing Asthma Symptoms [online] [retrieved on Apr. 23, 2010 from the internet] URL:http://www.webmd.com/asthma/guide/asthma-prevention.

Allergic Rhinitis—Prevention [online] [retrieved on Apr. 23, 2010 from the internet] URL:http://www.webmd.com/allergies/tc/allergic-rhinitis-prevention.

COPD Treatments: Improving Your Quality of Life [online] [retrieved on Apr. 23, 2010 from the internet] URL:http://www.webmd.com/lung/copd/copd-treatments-improving-your-quality-of-life.

RN 110624-55-0, retrieved from CAPLUS; retrieved on Apr. 7, 2008.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.
USPTO Final Office Action in U.S. Appl. No. 10/552,082, mailed Jun. 9, 2008, 18 pages.
Fish & Richardson P.C., Amendment in Reply to Action of Jun. 9, 2008 in U.S. Appl. No. 10/552,082, filed Sep. 9, 2008, 11 pages.
USPTO Office Action in U.S. Appl. No. 10/552,082, mailed Dec. 4, 2008, 23 pages.
Fish & Richardson P.C., Amendment in Reply to Action of Dec. 4, 2008 in U.S. Appl. No. 10/552,082, filed Apr. 6, 2009, 8 pages.
USPTO Notice of Allowance in U.S. Appl. No. 10/552,082, mailed Jul. 1, 2009, 9 pages.
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/552,082, mailed Jan. 7, 2010, 12 pages.
Fish & Richardson P.C., Amendment in Reply to Action of Jan. 7, 2010 in U.S. Appl. No. 10/552,082, filed Jul. 2, 2010, 8 pages.
USPTO Office Action in U.S. Appl. No. 10/551,783, mailed Dec. 7, 2009, 15 pages.
Fish & Richardson P.C., Amendment in Reply to Action of Dec. 7, 2009 in U.S. Appl. No. 10/551,783, filed Mar. 8, 2010, 17 pages.
USPTO Office Action in U.S. Appl. No. 10/551,783, mailed Apr. 23, 2010, 9 pages.
Fish & Richardson P.C., Amendment in Reply to Action of Apr. 23, 2010 in U.S. Appl. No. 10/551,783, filed Jul. 2, 2010, 23 pages.
USPTO Office Action in U.S. Appl. No. 10/569,065, mailed May 4, 2007, 12 pages.
Fish & Richardson P.C., Amendment in Reply to Action of May 4, 2007 in U.S. Appl. No. 10/569,065, filed Aug. 3, 2007, 14 pages.
USPTO Final Office Action in U.S. Appl. No. 10/569,065, mailed Oct. 17, 2007, 4 pages.
Fish & Richardson P.C., Amendment in Reply to Action of Oct. 17, 2007 in U.S. Appl. No. 10/569,065, filed Jan. 17, 2008, 9 pages.
USPTO Office Action in U.S. Appl. No. 10/569,065, mailed Apr. 16, 2008, 14 pages.
Fish & Richardson P.C., Amendment in Reply to Action of Apr. 16, 2008 in U.S. Appl. No. 10/569,065, filed Jul. 16, 2008, 38 pages.
USPTO Office Action in U.S. Appl. No. 10/569,065, mailed Oct. 28, 2008, 15 pages.
Fish & Richardson P.C., Amendment in Reply to Action of Oct. 28, 2008 in U.S. Appl. No. 10/569,065, filed Jan. 27, 2009, 7 pages.
USPTO Office Action in U.S. Appl. No. 10/569,065, mailed May 13, 2009, 10 pages.
Fish & Richardson P.C., Amendment in Reply to Action of May 13, 2009 in U.S. Appl. No. 10/569,065, filed Jul. 14, 2009, 9 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Final Office Action in U.S. Appl. No. 11/574,076, mailed Aug. 18, 2009, 7 pages.
Fish & Richardson P.C., RCE and Amendment in Reply to Action of Aug. 18, 2009 in U.S. Appl. No. 11/574,076, filed Dec. 18, 2009, 13 pages.
USPTO Notice of Allowance in U.S. Appl. No. 11/574,076, mailed Feb. 3, 2010, 12 pages.

Fish & Richardson P.C., Response to Notice of Allowance of Feb. 3, 2010 in U.S. Appl. No. 11/574,076, filed Apr. 30, 2010, 2 pages.
USPTO Office Action in U.S. Appl. No. 11/576,372, mailed Jul. 22, 2009, 19 pages.
Fish & Richardson P.C., Amendment in Reply to Action of Jul. 22, 2009 in U.S. Appl. No. 11/576,372, filed Jan. 22, 2010, 18 pages.
USPTO Final Office Action in U.S. Appl. No. 11/576,372, mailed May 7, 2010, 7 pages.
USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Notice of Allowance in U.S. Appl. No. 12/089,276, mailed Jan. 4, 2010, 6 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Office Action in U.S. Appl. No. 12/092,431, mailed Aug. 4, 2009, 8 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
USPTO Final Office Action in U.S. Appl. No. 12/167,513, mailed Apr. 22, 2010, 22 pages.
Berhenke et al., "Some Aryloxyaliphatic Acids", *Journal of the American Chemical Society* 73:4458 (1951).
Burger, "Isosterism and bioisosterism in drug design", in Progress in Drug Research 287-328 (Ernst Jucker, ed., Birkhauser Verlag, 1991).
Chemical abstract 123:213132 in CAS (or JP07140725), 1995.
Chemical abstract 123:22081 in CAS (or EP622690), 1995.
Chemical abstract 116:123167 in CAS (or EP455058), 1992.
Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1955).
Chemical abstract 35:37645 in CAS or Hazlet et al., "The Bromination of 2-Phenylphenyl Acetate", Journal of the American Chemical Society 63:1890-2 (1941).
Coxworth, "Synthesis of Chlorinated 2-(3-Benzofuranyl)Phenols", *Canadian Journal of Chemistry* 44:1092-1096 (1966).
"DialogWeb Records", http://www.dialogweb.com/cgi/document?req=1284661379410, accessed Sep. 16, 2010.
Hazlet et al., "The Bromination of 2-Phenylphenyl Acetate", *Journal of the American Chemical Society* 63:1890-1892 (1941).
Patani et al., "Bioisosterism: A Rational Approach in Drug Design", *Chem. Rev.* 96:3147-3176 (1996).
Database Beilstein chemical extract accession No. 6722243, Jan. 2010.
Database Beilstein chemical extract accession No. 6722682, Jan. 2010.

Database Beilstein chemical extract accession No. 3532059, Jan. 2010.
Database Beilstein chemical extract accession No. 2533336, Jan. 2010.
Database Beilstein chemical extract accession No. 2537173, Jan. 2010.
Database Beilstein chemical extract accession No. 3385275, Jan. 2010.
Database Beilstein chemical extract accession No. 3386554, Jan. 2010.
USPTO Notice of Allowance in U.S. Appl. No. 10/552,082, mailed Sep. 15, 2010, 12 pages.
USPTO Office Action in U.S. Appl. No. 10/551,783, mailed Sep. 7, 2010, 6 pages.
Fish & Richardson P.C., RCE and IDS in reply to Notice of Allowance of Sep. 7, 2010 in U.S. Appl. No. 10/551,783, filed Dec. 6, 2010, 4 pages.
USPTO Notice of Allowance in U.S. Appl. No. 10/569,065, mailed Sep. 1, 2010, 9 pages.
Fish & Richardson P.C., RCE and IDS in Reply to Notice of Allowance of Sep. 1, 2010 in U.S. Appl. No. 10/569,065, filed Nov. 8, 2010, 5 pages.
USPTO Notice of Allowance in U.S. Appl. No. 10/569,065, mailed Dec. 2, 2010, 10 pages.
Fish & Richardson P.C., RCE and IDS in Reply to Notice of Allowance of Dec. 2, 2010 in U.S. Appl. No. 10/569,065, filed Feb. 15, 2011, 5 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
Fish & Richardson P.C., RCE, IDS and Amendment in Reply to Action of Sep. 2, 2010 in U.S. Appl. No. 11/576,372, filed Dec. 2, 2010, 16 pages.
USPTO Office Action in U.S. Appl. No. 11/719,832, mailed Oct. 6, 2010, 12 pages.
Fish & Richardson P.C., RCE, IDS and Amendment in Reply to Action of Oct. 6, 2010 in U.S. Appl. No. 11/719,832, filed Apr. 6, 2011, 27 pages.
USPTO Office Action in U.S. Appl. No. 12/089,275, mailed Jan. 26, 2011, 25 pages.
USPTO Notice of Allowance in U.S. Appl. No. 12/089,276, mailed Sep. 21, 2010, 9 pages.
Fish & Richardson P.C., RCE and IDS in Reply to Notice of Allowance of Sep. 21, 2010 in U.S. Appl. No. 12/089,276, filed Dec. 20, 2010, 6 pages.
USPTO Notice of Allowance in U.S. Appl. No. 12/089,276, mailed Jan. 4, 2011, 11 pages.
Fish & Richardson P.C., RCE and IDS in Reply to Notice of Allowance of Jan. 4, 2011 in U.S. Appl. No. 12/089,276, filed Apr. 4, 2011, 4 pages.
Fish & Richardson P.C., RCE, IDS and Amendment in Reply to Action of May 4, 2010 in U.S. Appl. No. 12/092,431, filed Sep. 7, 2010, 16 pages.
Fish & Richardson P.C., Amendment in Reply to Action of Apr. 22, 2010 in U.S. Appl. No. 12/167,513, filed Oct. 22, 2010, 22 pages.

* cited by examiner

SUBSTITUTED ACIDS FOR THE TREATMENT OF RESPIRATORY DISEASES

CROSS-REFERENCE TO RELATED APPLICATIONS

This application is a national phase application under 35 U.S.C. 371 of PCT International Application No. PCT/GB2005/002650, filed Jul. 6, 2005, which claims priority to United Kingdom Application Serial No. 0415320.1, filed Jul. 8, 2004.

The present invention relates to substituted acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain acids are active at the CRTH2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

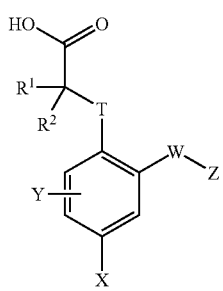

(I)

in which:

T is a bond, $S(O)_n$ (where n is 0, 1 or 2), $CR^1R^2$ or $NR^{13}$;

W is O, $S(O)_n$ (where n is 0, 1 or 2), $NR^{13}$, $CR^1OR^2$ or $CR^1R^2$;

X is hydrogen, halogen, cyano, nitro, $S(O)_nR^6$, $OR^{12}$ or $C_{1-6}$alkyl which may be substituted by one or more halogen atoms;

Y is selected from hydrogen, halogen, CN, nitro, $SO_2R^3$, $OR^4$, $SR^4$, $SOR^3$, $SO_2NR^4R^5$, $CONR^4R^5$, $NR^4R^5$, $NR^6SO_2R^3$, $NR^6CO_2R^6$, $NR^6COR^3$, $C_2-C_6$ alkenyl, $C_2-C_6$ alkynyl, $C_3-C_7$ cycloalkyl or $C_{1-6}$alkyl, the latter four groups being optionally substituted by one or more substituents independently selected from halogen, $OR^6$ and $NR^6R^7$, $S(O)_nR^6$ where n is 0, 1 or 2;

Z is aryl or heteroaryl, optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, $NR^6CONR^4R^5$, $NR^6SO_2NR^4R^5$, aryl, heteroaryl, $C_2-C_6$ alkenyl, $C_2-C_6$ alkynyl, $C_3-C_7$ cycloalkyl or $C_{1-6}$alkyl, the latter four groups being optionally substituted by one or more substituents independently selected from halogen, $C_3-C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$.

$R^1$ and $R^2$ independently represent a hydrogen atom, halogen, $C_2-C_6$ alkenyl, $C_2-C_6$ alkynyl, $C_3-C_7$ cycloalkyl or a $C_{1-6}$alkyl group, the latter four groups being optionally substituted by one or more substituents independently selected from halogen, $C_3-C_7$ cycloalkyl, $NR^6R^7$, $OR^6$, $S(O)_nR^6$ (where n is 0, 1 or 2);

or $R^1$ and $R^2$ together can form a 3-8 membered ring optionally containing one or more atoms selected from O, S, $NR^6$ and itself optionally substituted by one or more $C_1-C_3$ alkyl or halogen;

$R^3$ represents $C_3-C_7$ cycloalkyl, $C_{1-6}$alkyl, $C_2-C_6$ alkenyl or $C_2-C_6$ alkynyl all of which may be optionally substituted by one or more substituents independently selected from halogen, $C_3-C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

$R^4$ and $R^5$ independently represent hydrogen, $C_3-C_7$ cycloalkyl or $C_{1-6}$alkyl, the latter two groups being optionally substituted by one or more substituents independently selected from halogen, $C_3-C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^4$ and $R^5$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_{1-3}$ alkyl;

$R^6$ and $R^7$ independently represents a hydrogen atom or $C_1-C_6$ alkyl;

$R^8$ is hydrogen, $C_{1-4}$ alkyl, $—COC_1-C_4$ alkyl, $CO_2C_1-C_4$alkyl or $CONR^6C_1-C_4$alkyl;

$R^9$ represents aryl, heteroaryl, $C_3-C_7$ cycloalkyl or $C_{1-6}$alkyl, the latter two groups may be optionally substituted by one or more substituents independently selected from halogen, $C_3-C_7$ cycloalkyl, aryl, heteroaryl $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

$R^{10}$ and $R^{11}$ independently represent aryl or heteroaryl, hydrogen, $C_3-C_7$ cycloalkyl or $C_1-C_6$alkyl, the latter two groups being optionally substituted by one or more substituents independently selected from halogen, $C_3-C_7$ cycloalkyl, aryl, heteroaryl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^{10}$ and $R^{11}$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_1-C_3$ alkyl, $R^{12}$ represents a hydrogen atom or $C_1-C_6$alkyl which may be substituted by one or more halogen atoms, and $R^{13}$ represents a hydrogen atom, $C_{1-6}$alkyl which may be substituted by one or more halogen atoms or $C_3-C_7$ cycloalkyl, $SO_2R^6$ or $COC_1-C_4$ alkyl, provided that when T is carbon or a bond, the substituent on group Z cannot be $NR^{10}R^{11}$, where $R^{10}R^{11}$ are independently hydrogen, aryl, or alkyl, and the compounds 2-[(4-carboxyphenyl)amino]-4,5-dihydroxy-benzenepropanoic acid and 4-chloro-2-[(4-chlorophenyl)thio]-benzeneacetic acid are excluded.

Examples of aryl include phenyl and naphthyl.

Heteroaryl is defined as a 5-7 member aromatic ring or can be 6,6- or 6,5-fused bicyclic ring optionally containing one or more heteroatoms selected from N, S, O. The bicyclic ring may be linked through carbon or nitrogen and may be attached through the 5 or 6 membered ring and can be fully or partially saturated.

Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine and quinolone.

Aryl or heteroaryl groups can be optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, $NR^6CONR^4R^5$, $NR^6SO_2NR^4R^5$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$.

In the context of the present specification, unless otherwise indicated, an alkyl or alkenyl group or an alkyl or alkenyl moiety in a substituent group may be linear or branched.

Heterocyclic rings as defined for $R^4$, $R^5$ and $R^{10}$ and $R^{11}$ means saturated heterocycles, examples include morpholine, azetidine, pyrrolidine, piperidine and piperazine.

Preferably X is trifluoromethyl or halogen, in particular chloro and fluoro.

Preferably Y is hydrogen or $C_{1-6}$alkyl, such as methyl. More preferably Y is hydrogen.

Preferably Z is phenyl, optionally substituted as defined above. Preferred substituents for all Z groups include those substituents exemplified herein, in particular heteroaryl, aryl halogen, $SO_2R^9$, $CF_3$ and CN. More preferably the substituents are halogen, $SO_2R^9$ where $R^9$ is methyl or ethyl, $CF_3$ or CN. Most preferably Z is phenyl substituted by two substituents, one of which is $SO_2R^9$ where $R^9$ is methyl or ethyl, and the other is halogen, preferably chloro fluoro, or $CF_3$.

Preferably $R^1$ and $R^2$ are independently hydrogen or $C_{1-3}$ alkyl. More preferably $R^1$ and $R^2$ are independently hydrogen or methyl. Most preferably $R^1$ and $R^2$ are both hydrogen.

Preferably, W is O, $S(O)_n$ (where n is 0, 1 or 2), $NR^{13}$, $CR^1R^2$. More preferably W is O, S, NH or $CH_2$. Most preferably W is O, S or NH. Even more preferably W is O;

Preferably, T is a bond, S, $CR^1R^2$ or $NR^{13}$. More preferably T is a bond, S, $CR^1R^2$ where $R^1$, $R^2$ are independently hydrogen or methyl, or T is an NH group.

Most preferably T is a bond, $CH_2$, or NH.

Preferred compounds of the invention include:
N-(4-Chloro-2-phenoxyphenyl)glycine;
3-[2-(3-Cyanophenoxy)-4-(trifluoromethyl)phenyl]propanoic acid;
3-[2-[2-Chloro-4-(methylsulfonyl)phenoxy]-4-(trifluoromethyl)phenyl]propanoic acid;
3-[2-[2-Chloro-4-(ethylsulfonyl)phenoxy]-4-(trifluoromethyl)phenyl]propanoic acid;
[(4-Chloro-2-{[2-chloro-4-(ethylsulfonyl)phenyl]thio}phenyl)thio]acetic acid;
N-{4-Chloro-2-[2-chloro-4-(ethylsulfonyl)phenoxy]phenyl}glycine;
({4-Chloro-2-[2-chloro-4-(ethylsulfonyl)phenoxy]phenyl}thio)acetic acid;
3-{2-[2-Chloro-4-(methylsulfonyl)phenoxy]-4-fluorophenyl}propanoic acid;
{2-[2-Chloro-4-(methylsulfonyl)phenoxy]-4-fluorophenyl}acetic acid;
4-chloro-2-[2-chloro-4-(methylsulfonyl)phenoxy]-α-methyl-benzenepropanoic acid;
N-[2-[2-chloro-4-(methylsulfonyl)phenoxy]-4-fluorophenyl]-glycine;
N-[2-[2-chloro-4-(ethylsulfonyl)phenoxy]-4-fluorophenyl]-glycine;
N-[2-[2-chloro-4-(methylsulfonyl)phenoxy]-4-fluorophenyl]-2-methyl-alanine;
N-[2-[2-chloro-4-(methylsulfonyl)phenoxy]-4-fluorophenyl]-D-alanine;
N-[4-chloro-2-[2-chloro-4-(methylsulfonyl)phenoxy]phenyl]-glycine;
[[4-chloro-2-[2-chloro-4-(methylsulfonyl)phenoxy]phenyl]thio]-acetic acid;
N-[2-[2-chloro-4-(ethylsulfonyl)phenoxy]-4-fluorophenyl]-D-alanine;
N-[4-chloro-2-[2-chloro-4-(methylsulfonyl)phenoxy]phenyl]-D-alanine;
N-[4-chloro-2-[2-chloro-4-(methylsulfonyl)phenoxy]phenyl]-N-methyl-glycine;
2-[2-chloro-4-(ethylsulfonyl)phenoxy]-4-fluoro-benzenepropanoic acid;
2-[4-(ethylsulfonyl)-3-(trifluoromethyl)phenoxy]-4-fluoro-benzenepropanoic acid;
2-[4-(ethylsulfonyl)-3-(trifluoromethyl)phenoxy]-4-fluoro-benzenepropanoic acid;
N-[4-chloro-2-[[4-(ethylsulfonyl)phenyl]thio]phenyl]-glycine;
N-[4-chloro-2-[[4-(ethylsulfonyl)phenyl]thio]phenyl]-D-alanine;
N-[4-chloro-2-[4-(ethylsulfonyl)-3-(trifluoromethyl)phenoxy]phenyl]-glycine;
N-[4-chloro-2-[4-(ethylsulfonyl)-3-(trifluoromethyl)phenoxy]phenyl]-D-alanine;
N-[2-[2-chloro-4-(ethylsulfonyl)phenoxy]-4-(trifluoromethyl)phenyl]-glycine;
N-[2-[4-(ethylsulfonyl)-3-(trifluoromethyl)phenoxy]-4-(trifluoromethyl)phenyl]-glycine;
N-[4-chloro-2-(2-chloro-4-cyanophenoxy)phenyl]-glycine;
N-[2-(4-bromo-2-chlorophenoxy)-4-chlorophenyl]-glycine;
N-[4-chloro-2-[2-chloro-4-(5-methyl-1,2,4-oxadiazol-3-yl)phenoxy]phenyl]-glycine;
N-[4-chloro-2-[2-chloro-4-(5-ethyl-1,2,4-oxadiazol-3-yl)phenoxy]phenyl]-glycine;
N-[4-chloro-2-[2-chloro-4-(5-pyrimidinyl)phenoxy]phenyl]-glycine;
N-[4-chloro-2-[2-chloro-4-(2-pyridinyl)phenoxy]phenyl]-glycine;
4-chloro-2-[2-chloro-4-(ethylsulfonyl)phenoxy]-benzenepropanoic acid;
4-chloro-2-[2-cyano-4-(ethylsulfonyl)phenoxy]-benzenepropanoic acid;
N-(4-Chloro-2-{2-chloro-4-[(ethylsulfonyl)amino]phenoxy}phenyl)glycine;
N-{4-Chloro-2-[3-chloro-4-(trifluoromethyl)phenoxy]phenyl}glycine;
N-{4-Chloro-2-[4-cyano-2-(trifluoromethyl)phenoxy]phenyl}glycine;
N-{4-Chloro-2-[2-cyano-4-(trifluoromethyl)phenoxy]phenyl}glycine;
N-{4-Chloro-2-[4-[(methylsulfonyl)amino]-2-(trifluoromethyl)phenoxy]phenyl}glycine;
N-{4-Chloro-2-[4-[methyl(methylsulfonyl)amino]-2-(trifluoromethyl)phenoxy]phenyl}glycine;
4-chloro-2-[4-(ethylsulfonyl)-2-(trifluoromethyl)phenoxy]-benzenepropanoic acid;
4-chloro-2-[4-(methylsulfonyl)-2-(trifluoromethyl)phenoxy]-benzenepropanoic acid;
4-fluoro-2-[4-(methylsulfonyl)-2-(trifluoromethyl)phenoxy]-benzenepropanoic acid;
2-[4-(ethylsulfonyl)-2-(trifluoromethyl)phenoxy]-4-fluoro-benzenepropanoic acid;

2-[2-cyano-4-(ethylsulfonyl)phenoxy]-4-fluoro-benzenepropanoic acid;
2-[2-cyano-4-(methylsulfonyl)phenoxy]-4-fluoro-benzenepropanoic acid;
4-chloro-2-[[2-chloro-4-(methylsulfonyl)phenyl]amino]-benzenepropanoic acid;
4-chloro-2-[[2-chloro-4-(ethylsulfonyl)phenyl]amino]-benzenepropanoic acid;
4-chloro-2-[[2-chloro-4-(methylsulfonyl)phenyl]amino]-benzenepropanoic acid;
4-chloro-2-[[2-chloro-4-(ethylsulfonyl)phenyl]amino]-benzenepropanoic acid;
4-chloro-2-[4-(methylsulfonyl)-2-(trifluoromethyl)phenoxy]-benzeneacetic acid;
4-chloro-2-[[4-(methylsulfonyl)-2-(trifluoromethyl)phenyl]thio]-benzene propanoic acid;
4-chloro-2-[2-fluoro-4-(methylsulfonyl)phenoxy]-benzenepropanoic acid,
4-chloro-2-[2-chloro-4-(methylsulfonyl)phenoxy]-benzenepropanoic acid,
and pharmaceutically acceptable salts thereof.

Certain compounds of formula (I) are capable of existing in stereoisomers forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chlorprocaine, choline, diethanolamine, ethanolamine, ethyldiamine, meglumine, tromethamine, tertiary-butylamine and procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by reaction of a compound of formula (II):

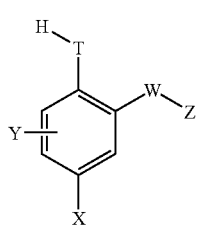

(II)

in which T=S or $NR^{13}$ and W, X, Y and Z are as defined in formula (I) or are protected derivatives thereof, with a compound of formula (III):

(III)

Where $R^1$ and $R^2$ are as defined in formula (I) or are protected derivatives thereof, $R^{14}$ is H or $C_1$-$C_{10}$ alkyl group and L is a leaving group, and optionally thereafter in any order:
removing any protecting group
hydrolysing the ester group $R^{14}$ to the corresponding acid
oxidation of sulphides to sulphoxides or sulphones
forming a pharmaceutically acceptable salt.

The reaction can be carried out in a suitable solvent such as ethanol using a base such as sodium acetate, carbonate or the like. Suitable groups $R^{14}$ include $C_{1-6}$ alkyl groups such as methyl, ethyl or tert-butyl. Suitable L is a leaving group such as triflate or halo, in particular chlorine or bromine. L may also be hydroxy so that a Mitsunobu reaction may be performed with compound (II) using for example triphenylphosphine and diethyl azodicarboxylate.

Hydrolysis of the ester group $R^{14}$ can be carried out using routine procedures, for example treatment of methyl and ethyl esters with aqueous sodium hydroxide, and treatment of tert-butyl esters with acids such as trifluoroacetic acid.

Compounds of formula (I) can be prepared by reaction of a compound of formula (IV) with a compound of formula (V):

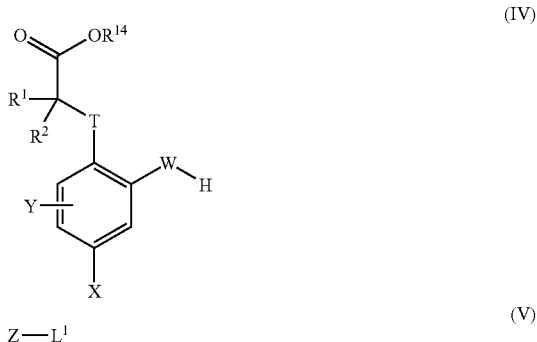

in which $R^1$, $R^2$, X, Y and Z are as defined in formula (I) or are protected derivatives thereof and W=S, $NR^{13}$ or O. $L^1$ is halogen, activated alcohol such as triflate or alkyl sulphone or sulphoxide.

The reaction can be carried out in a suitable solvent such as 1-methyl-2-pyrrolidinone with a base such as potassium carbonate, preferably at elevated temperatures.

Compounds of formula (I), where T=S may be prepared by reaction of a compound of formula (VI) with a diazotising agent and a compound of formula (VII), followed by removal of any protecting groups:

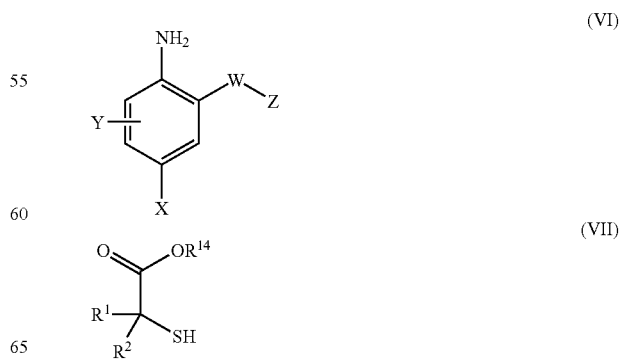

The reaction can be carried out in a suitable solvent such as acetonitrile using isoamylnitrite to form the diazonium, then reaction with ethyl mercaptoacetate, preferably at elevated temperatures.

Compounds of formula (VI) may be prepared using the general route A:

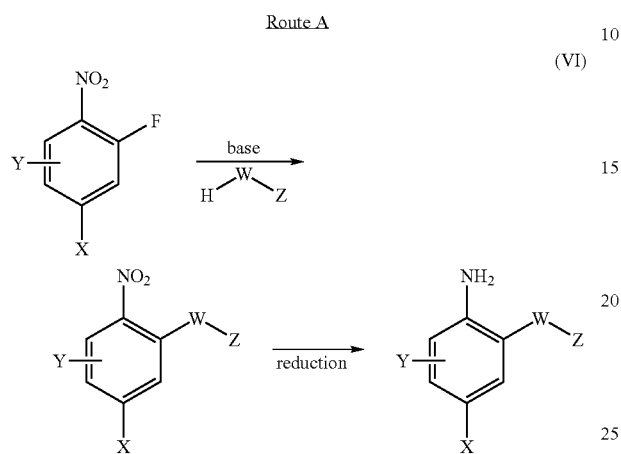

in which W=O, S or $NR^{13}$ and X, Y and Z are as defined in formula (I) or are protected derivatives thereof. The first step can be carried out in a suitable solvent such as DMF with a base such as potassium carbonate, preferably at elevated temperatures. The nitro group can then be reduced to the aniline using a suitable reducing agent such as iron in acetic acid or hydrogenation.

The steps can be reversed as outlined in Route A (i):

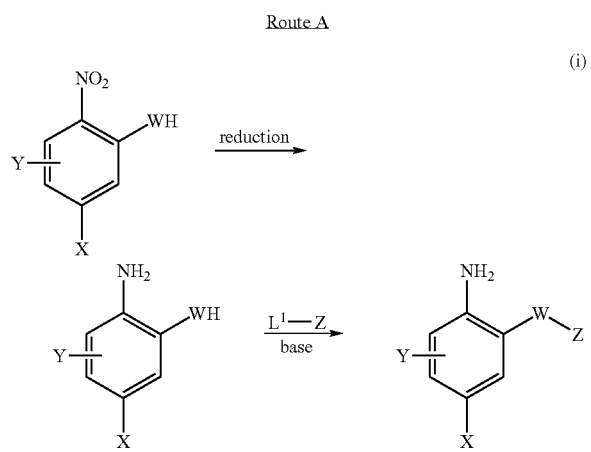

in which $L^1$ is a leaving group, W=O, S or $NR^{13}$ and X, Y and Z are as defined in formula (I) or are protected derivatives thereof. The nitro group is reduced first to the aniline using a suitable reducing agent such as iron in acetic acid or hydrogenation. The second step introduces the group 'Z', which can be carried out in a suitable solvent such as DMF with a base such as potassium carbonate, preferably at elevated temperatures.

Compounds of formula (I), where $T=CR^1R^2$, may be prepared using the general route B:

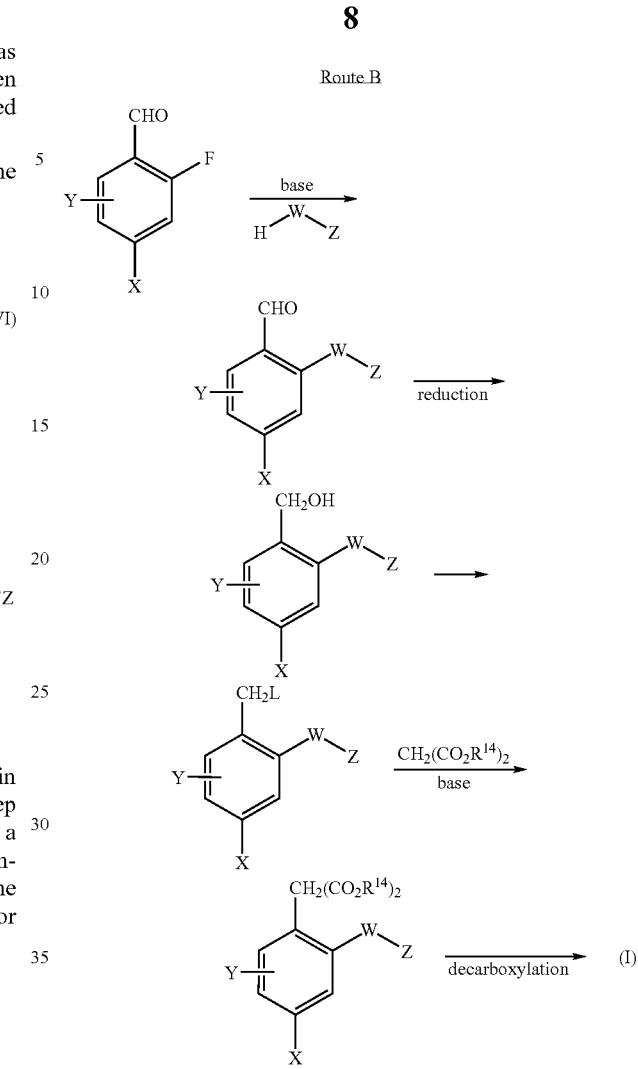

in which L is a leaving group, W=O, S or $NR^{13}$ and X, Y and Z are as defined in formula (I) or are protected derivatives thereof. The first step can be carried out in a suitable solvent such as DMF with a base such as potassium carbonate, preferably at elevated temperatures. The formyl group can then be reduced to the alcohol using a suitable reducing agent such as sodium borohydride in ethanol. The alcohol can be converted into a leaving group such as a mesylate, using methanesulphonyl chloride and triethylamine and displaced with the anion of a dialkylmalonate. The diester can be decarboxylated with sodium chloride in DMSO/water at elevated temperatures.

Certain compounds of formula (IV), where $T=CR^1R^2$ and W=O may be prepared using the general route B (i):

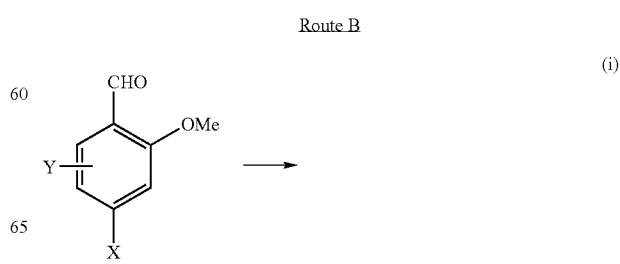

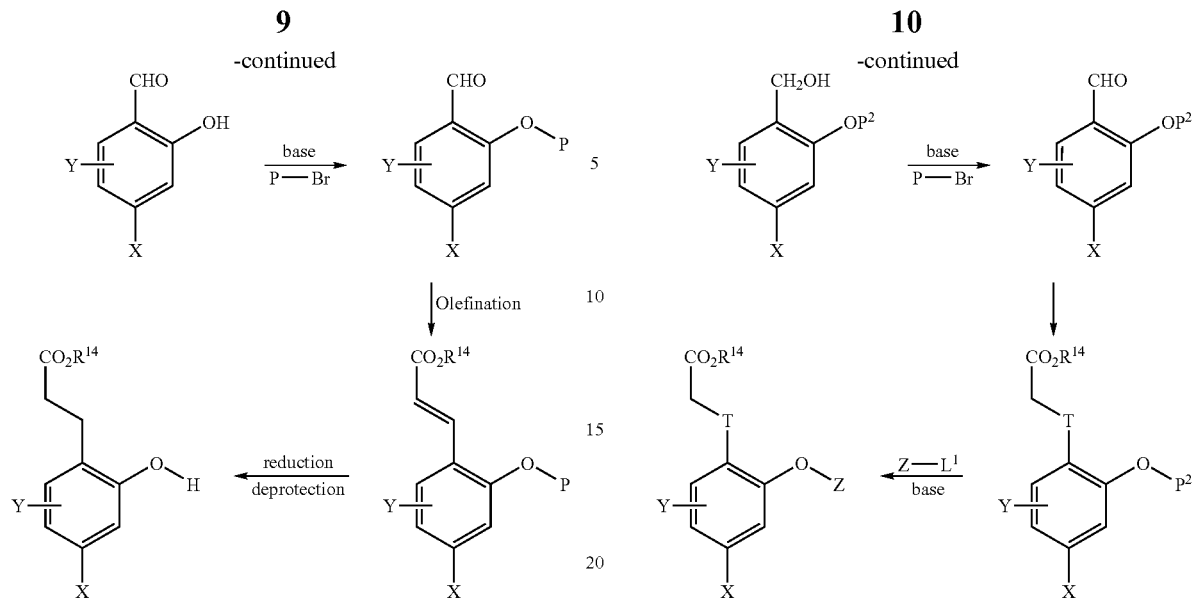

in which X, Y and Z are as defined in formula (I) or are protected derivatives thereof. P is a protecting group such as benzyl. The first step can be carried out in a suitable solvent such as DMF with a dealkylating agent such as lithium chloride, preferably at elevated temperatures. The alcohol group can then be protected using a suitable protecting reagent such as bromobenzyl The formyl group can be converted into an alkene using the Horner-Wadsworth Emmons procedure, reacting with a phosphonate group in the presence of a suitable base such as sodium hydride. The corresponding alkene is reduced and the protecting group removed in one step using a suitable reduction method such as hydrogenation.

Some compounds of formula (IV), where T=$CR^1R^2$ can be prepared by general method B (ii):

Route B

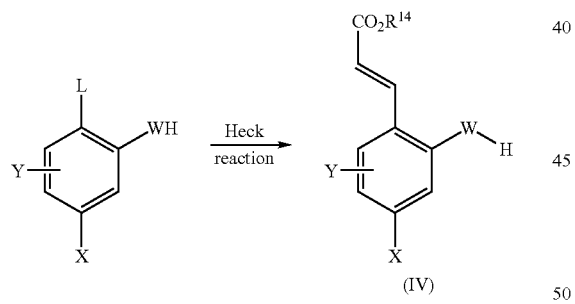

(IV)

in which L is a leaving group, W, X, Y and Z are as defined in formula (I) or are protected derivatives thereof. The first reaction can be carried out with a suitable alkene using a palladium catalyst, in a suitable solvent such as DMF.

Some compounds of formula (I), where T=$CR^1R^2$ and W is O, can be prepared by general method B (iii):

Route B (iii)

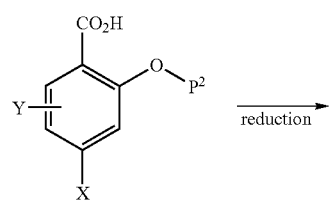

In which X, Y and Z are as defined in formula (I) or are protected derivatives thereof. $P^2$ can be hydrogen, methyl or an alcohol protecting group. The first step can be carried with a suitable reducing agent such as borane in a solvent such as THF at elevated temperatures.

The alcohol is then converted to the aldehyde in the presence of a suitable oxidising agent such as manganese dioxide. The propanoic acid is formed by reaction with triethylamine and Formic acid and then Meldram's acid in a suitable solvent such as DMF at elevated temperatures. The group Z is introduced as described in route A (i). The protecting group $P^2$ or when $P^2$ is alkyl, may be removed at any stage in the sequence using methods described in Route B (i) or known literature procedures. The sequence of steps can also be reversed, for example the group Z can be added as the first step in the sequence.

Compounds of formula (I), where T=$CR^1R^2$, and W=N may be prepared using the general route B (iv):

Route B (iv)

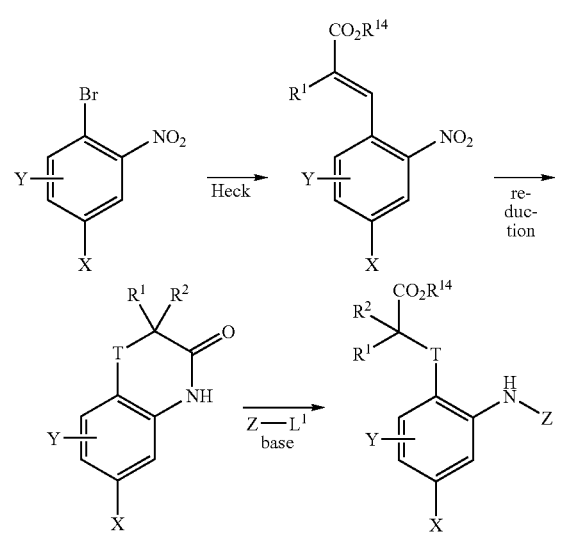

in which $L^1$ is a leaving group (as defined in (V)), X, Y and Z are as defined in formula (I) or are protected derivatives thereof. The first step is a Heck Reaction as outlined for Route B (ii). The product is then reduced using a suitable reagent such as Platinum on Charcoal. The group Z is then added in the presence of a base such as sodium hydride.

Compounds of formula (I) where T=NR$^{13}$, can be prepared using general route C:

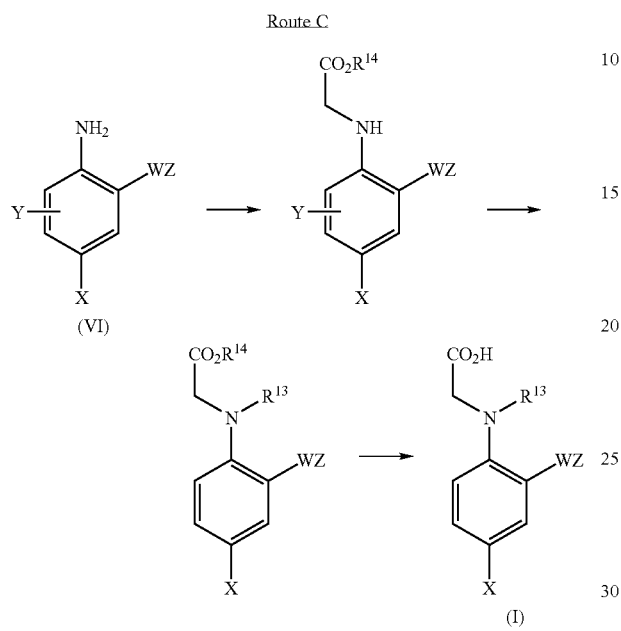

in which X, Y and Z are as defined in formula (I) or are protected derivatives thereof.

Compound VI is alkylated as described earlier. The nitrogen atom can be alkylated using dimethyl sulfate in the presence of base such as sodium bicarbonate at elevated temperatures to give compounds of formula (II). The ester is deprotected using a suitable base such as hydroxide to give compounds of formula (I). The group (VI) can be prepared as outlined in Route A.

The group Z-L$^1$, where the substituent=SO$_2$R$^9$ can be prepared by general Route D:

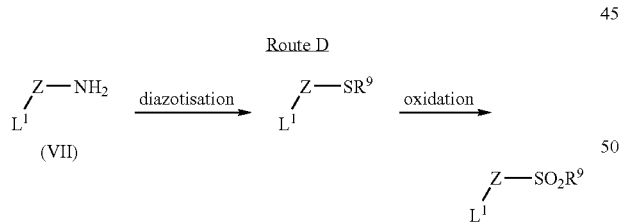

in which L$^1$=a leaving group as defined in (V). R$^9$ and Z are as defined in formula (I) or are protected derivatives thereof. Compounds of formula (VII) are diazotised using a reagent such as isoamylnitrite, then reacted with R$^9$S—SR$^9$, preferably at elevated temperatures. The product is then oxidised using a reagent such as oxone or meta-chloroperbenzoic acid in a chlorinated solvent such as dichloromethane or the like. Compounds of formula (VII) are commercially available or can be prepared by those skilled in the art using literature procedures.

Compounds of formula (VI), where the group Z has a substituent=aryl or heteroaryl can be prepared by general Routes D (i) or D(ii):

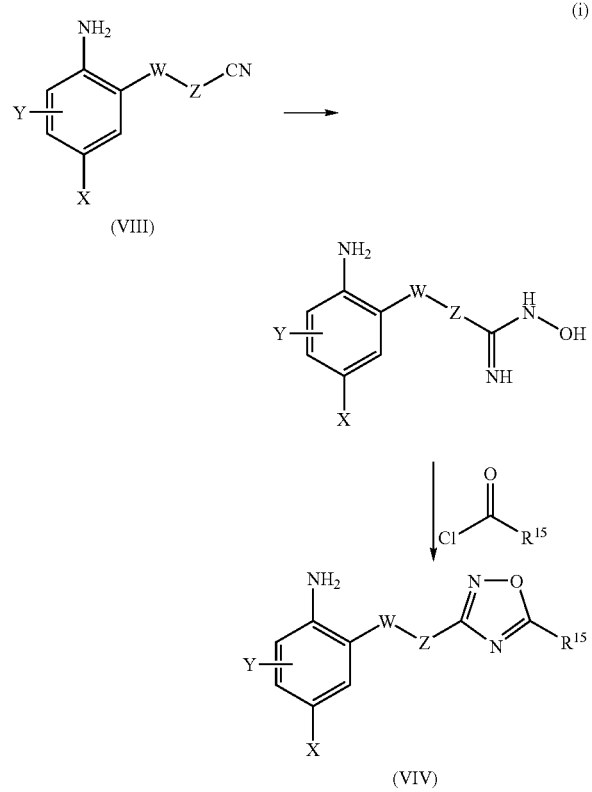

in which W, X, Y, Z and R$^{14}$ are as defined in formulas (I) and (II) or are protected derivatives thereof. R$^{15}$ is alkyl. Compounds of formula (VIII) can be prepared by methods outlined in Route A as described for compounds of formula (VI). The compounds of formula (VIII) are treated with hydroxylamine and a suitable base such as carbonate at elevated temperatures.

The resulting product is treated with an acid chloride in the presence of a base, such as pyridine, to give the desired heterocycle in compounds of formula (VIV):

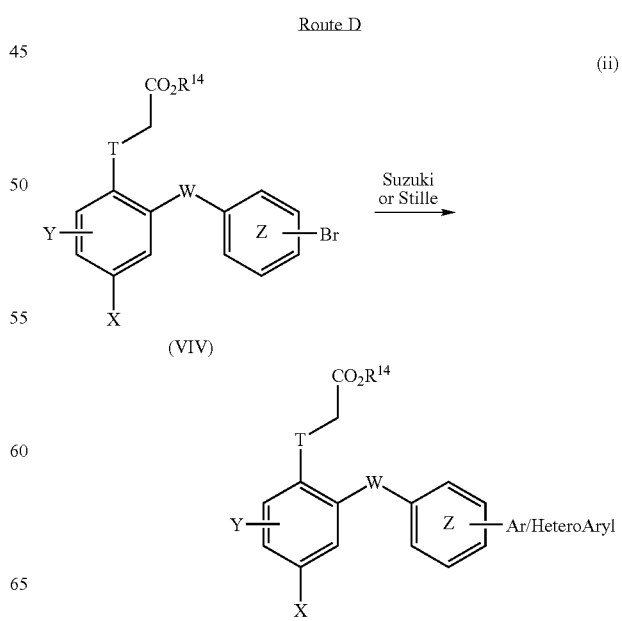

in which T, W, X, Y, Z and $R^{14}$ are as defined in formula (I) or are protected derivatives thereof. The compounds of formula (VIV) can be reacted with either a Boronic acid or Organostannane using a suitable catalyst such as $Pd(dppf)Cl_2$ in the presence of a base such as caesium fluoride at elevated temperatures, in a solvent such as dioxan.

Compounds of formula (I) where T is a bond can be prepared by general method E:

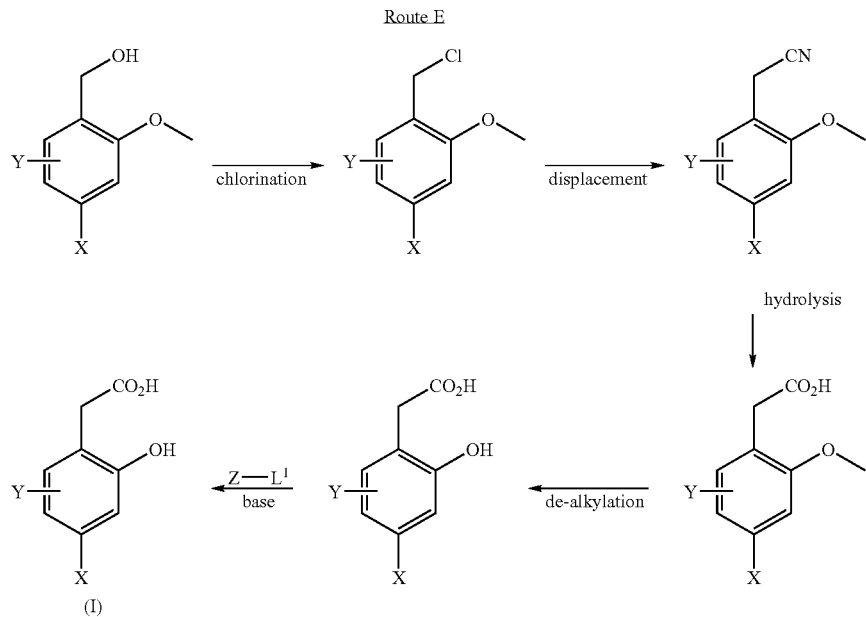

in which X, Y, and Z are as defined in formula (I) or are protected derivatives thereof. $L^1$=a leaving group as defined in (V). The first step can be carried out using a chlorinating agent such as thionyl chloride, in a suitable solvent such as dichloromethane. This can be converted to the nitrile using a suitable reagent such as sodium cyanide in a polar solvent such as DMF at elevated temperatures. The acid group can be formed using a strong base, such as hydroxide, suitably potassium hydroxide. The ether group can be cleaved using suitable dealkylation conditions, such as heating in a mixture of hydrobromic acid and acetic acid. The group $Z-L^1$ is introduced as described in route A (i)

In a further aspect, the present invention provides the use of a compound of formula (I), pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinophilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, and unless otherwise stated the mass ion quoted is the positive mass ion—(M+H)$^+$;

(iii) the title compounds of the examples and methods were named using the ACD/name (version 6.0) from Advanced Chemical Development Inc, Canada;

(iv) unless stated otherwise, reverse phase HPLC was conducted using a Symmetry, NovaPak or Ex-Terra reverse phase silica column;

(v) solvents were dried with $MgSO_4$ or $Na_2SO_4$ (vi) the following abbreviations are used:

EtOAc Ethylacetate

DCM Dichloromethane h hours

HPLC high performance liquid chromatography

NMP N-methylpyrrolidine

DMF N,N-dimethylformamide

THF tetrahydrofuran mcpba 3-chloroperoxybenzoic acid (Aldrich 77% max)

Pd(dppf)Cl$_2$ [1,1'-Bis(diphenylphosphino)ferrocene] dichloropalladium(II), complex with dichloromethane RT room temperature

EXAMPLE 1

N-(4-Chloro-2-phenoxyphenyl)glycine

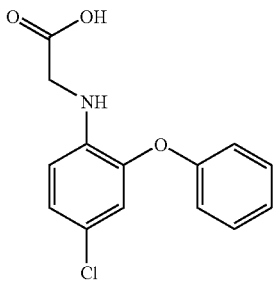

(i) 4-Chloro-2-phenoxyaniline

2-Fluoro-4-chloro-nitrobenzene (0.50 g), phenol (0.27 g) and potassium carbonate (0.40 g) in dry DMSO (10 ml) were stirred at RT for 2 h. The mixture was diluted with water, extracted with diethylether, dried and evaporated under reduced pressure to give a yellow oil (0.90 g). The oil was dissolved in glacial acetic acid (20 ml) and treated with reduced iron powder (0.90 g). The mixture was vigorously stirred at RT for 2 h, filtered through celite, washed with DCM and the filtrate evaporated under reduced pressure, yield 0.9 g.

MS: ESI (+ve) 220 (M+1)

(ii) N-(4-Chloro-2-phenoxyphenyl)glycine

A mixture of the product from step (i) (0.9 g), t-butyl-bromoacetate (0.8 ml) and sodium acetate (0.5 g) in ethanol (20 ml) was heated under reflux for 20 h, cooled and evaporated under reduced pressure. The residue was dissolved in ethyl acetate, washed with water, dried and evaporated under reduced pressure to give an orange oil (1.4 g). The oil was dissolved in trifluoroacetic acid/DCM 1:1 (20 ml), stirred at RT for 24 h then evaporated under reduced pressure. The residue was purified by reverse phase HPLC, yield 0.149 g.

1H NMR DMSO-d6: δ 7.40-7.36 (2H, m), 7.15-7.11 (1H, m), 7.06-6.96 (3H, m), 6.76 (1H, s), 6.63-6.61 (1H, d), 5.56 (1H, m), 3.86 (2H, s).

MS: APCI (−ve) 276 (M−1)

EXAMPLE 2

3-[2-(3-Cyanophenoxy)-4-(trifluoromethyl)phenyl]propanoic acid

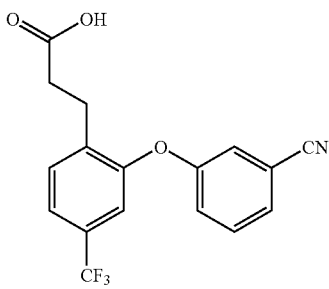

(i) 3-[2-Formyl-5-(trifluoromethyl)phenoxy]benzonitrile

A mixture of 4-(1,1,1-trifluoromethyl)-2-fluoro-benzaldehyde (2.5 g), potassium carbonate (1.79 g) and 3-cyanophenol (1.54 g) in DMF (20 ml) was heated at 110° C. for 2 h then cooled. Water (200 ml) was added and the mixture extracted with ethyl acetate, dried and evaporated under reduced pressure. The residue was purified by chromatography on silica eluting with isohexane/diethylether 2:1 to give a colourless oil, yield 2.0 g.

MS: ESI (−ve) 290 (M−1)

(ii) 3-[2-(Hydroxymethyl)-5-(trifluoromethyl)phenoxy]benzonitrile

The product from step (i) (2.0 g) was dissolved in dry ethanol (20 ml) then sodium borohydride (0.15 g) added. The mixture was stirred at RT overnight then evaporated under reduced pressure to give a white solid. The solid was partitioned between 2M hydrochloric acid and ethylacetate, the organics were dried and evaporated under reduced pressure, yield 0.70 g.

1H NMR CDCl₃: δ 7.73-7.66 (1H, m), 7.52-7.39 (3H, m), 7.23-7.18 (2H, m), 7.11-7.08 (1H, m), 4.81-4.79 (2H, s), 1.91 (1H, bs).

(iii) 2-(3-Cyanophenoxy)-4-(trifluoromethyl)benzyl methanesulfonate

Triethylamine (0.33 ml) followed by methanesulphonyl chloride (0.185 ml) were added to a solution of the product from step (ii) (0.7 g) in DCM (20 ml) at −20° C. The mixture was stirred at 0° C. for 1 h, then diluted with dichloromethane, washed with water, dried and evaporated under reduced pressure, yield 0.97 g.

MS: ESI (−ve) 278 (M-OMs)

(iv) Diethyl [2-(3-cyanophenoxy)-4-(trifluoromethyl)benzyl]malonate

Sodium hydride (60% wt. disp. oil, 0.105 g) was added to a solution of diethylmalonate (0.40 ml) in dry THF (20 ml) at 0° C. The mixture was stirred at RT for 30 min, cooled to 0° C., then a solution of the product from step (iii) (0.97 g) in THF (10 ml) was added. The mixture was stirred at RT overnight, water was added and the mixture extracted with diethylether. The organics were dried and evaporated under reduced pressure to give an oil which was purified by chromatography on silica eluting with isohexane/diethylether 2:1. Yield 0.6 g.

MS: ESI (−ve) 434 (M−1)

(v) 3-[2-(3-Cyanophenoxy)-4-(trifluoromethyl)phenyl]propanoic acid

Sodium chloride (0.1 g) was added to a solution of the product from step (iv) (0.6 g) in DMSO (5 ml) and water (1 ml) then heated at 120° C. for 12 hours. The mixture was cooled and partitioned between 2M sodium hydroxide and diethylether. The aqueous layer was acidified with 2M hydrochloric acid, extracted with ethyl acetate and the organic layer dried and evaporated under reduced pressure. The residue was purified by reverse phase HPLC. Yield 0.108 g.

1H NMR: DMSO-d6: δ 7.35-7.32 (1H, m), 7.65-7.54 (5H, m), 7.25-7.24 (1H, s), 2.89-2.85 (2H, t), 2.59-2.51 (2H, t).

MS: ESI (−ve) 334 (M−1)

EXAMPLE 3

3-[2-[2-Chloro-4-(methylsulfonyl)phenoxy]-4-(trifluoromethyl)phenyl]propanoic acid

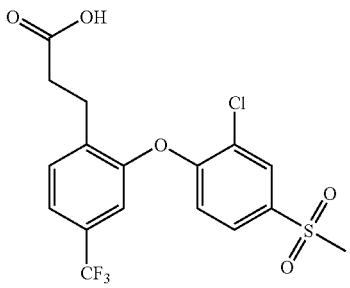

(i) 2-Methoxy-4-(trifluoromethyl)benzaldehyde

A solution of sodium methoxide (25% wt in methanol, 50 ml) was added to a solution of (4-(1,1,1-trifluoromethyl)-2-fluoro-benzaldehyde (5.0 g) in methanol (50 ml) and the mixture heated under reflux for 2 h. Water (200 ml) was added and the mixture extracted with ethyl acetate. The organics were dried and evaporated under reduced pressure to give a residue that was purified by chromatography on silica eluting with isohexane/diethylether 3:1, yield 3.18 g.

1H NMR CDCl$_3$: δ 7.94-7.92 (1H, d), 7.31-7.22 (2H, m), 4.00 (3H, s).

(ii) 2-Hydroxy-4-(trifluoromethyl)benzaldehyde

A mixture of the product from step (i) (3.18 g) and lithium chloride (1.96 g) in DMF (30 ml) was heated at 150° C. for 5 h. The mixture was partitioned between diethylether and 2M hydrochloric acid, the organic layer dried, and the solvent evaporated under reduced pressure. The residue was purified by chromatography on silica eluting with isohexane/diethylether 3:1, yield 2.30 g.

MS: ESI (–ve) 189 (M–1)

(iii) 2-(Benzyloxy)-4-(trifluoromethyl)benzaldehyde

A mixture of the product from step (ii) (2.3 g), benzyl bromide (1.44 ml) and potassium carbonate (1.67 g) in DMF (20 ml) was stirred at RT for 2 h. The mixture was partitioned between diethylether and water, the organic layer dried, and the solvent evaporated under reduced pressure. The residue was purified by chromatography on silica eluting with 40/60 pet. ether/diethylether 4:1, yield 2.83 g.

1H NMR CDCl$_3$: δ 10.56-10.55 (1H, s), 7.97-7.96 (1H, d), 7.47-7.25 (7H, m), 5.23 (2H, s).

(iv) tert-Butyl (2E)-3-[2-(benzyloxy)-4-(trifluoromethyl)phenyl]acrylate

Sodium hydride (60% wt. disp. oil, 0.406 g) was added to a solution of tert-butyl-P,P-dimethylphosphonoacetate (2.27 g) in dry DMF (20 ml) at 0° C. The mixture was stirred at RT for 30 min, cooled to 0° C., then the product from step (iii) (2.83 g) added. After 16 h the mixture was partitioned between diethylether and water, the organic layer dried, and the solvent evaporated under reduced pressure. The residue was purified by chromatography on silica eluting with isohexane/diethylether 4:1, yield 3.25 g.

1H NMR CDCl$_3$: δ 7.98-7.93 (1H, d), 7.63-7.18 (8H, m), 6.52-6.46 (1H, d), 5.18 (2H, s), 1.52 (9H, s).

(v) tert-Butyl 3-[2-hydroxy-4-(trifluoromethyl)phenyl]propanoate

A mixture of the product from step (iv) (3.25 g) and 10% palladium on carbon (0.325 g) in ethanol (40 ml) was hydrogenated at a pressure of 3.0 bar overnight. The mixture was filtered through celite and the filtrate concentrated under reduced pressure to give a white solid (2.22 g).

MS: ESI (–ve) 289 (M–1)

(vi) 3-Chloro-4-fluorophenyl methyl sulfide

Iodomethane (1.15 ml) was added to a stirred mixture of 3-chloro-4-fluoro-benzenethiol (3.0 g) and potassium carbonate (2.48 g) in DMF (20 ml) and left overnight. The reaction was diluted with water and extracted with diethylether, the organics were dried and evaporated under reduced pressure, yield 4.3 g.

1H NMR CDCl$_3$: δ 7.31-7.14 (2H, m), 7.13-7.03 (1H, m), 3.23-3.21 (3H, s).

(vii) 3-Chloro-4-fluorophenyl methyl sulfone

3-Chloroperoxybenzoic acid (70% purity, 10.75 g) was added to a solution of the product from step (vi) (4.3 g) in DCM (100 ml) and stirred at RT for 2 h. The mixture was partitioned between DCM/aq. sodium metabisulphite solution, the organics washed with aq. sodium hydrogencarbonate solution, water, dried and evaporated under reduced pressure. Yield 4.0 g 1H NMR CDCl$_3$: δ 8.06-8.03 (1H, m), 7.89-7.84 (1H, m), 7.38-7.32 (1H, m), 3.08 (3H, s).

(viii) 3-[2-[2-Chloro-4-(methylsulfonyl)phenoxy]-4-(trifluoromethyl)phenyl]propanoic acid A mixture of the product from step (v) (0.6 g), the product from step (vii) (0.43 g) and potassium carbonate (0.285 g) in NMP (10 ml) was heated at 70° C. for 4 h. The mixture was partitioned between diethylether and water, the organic layer dried, and the solvent evaporated under reduced pressure. The residue was dissolved in 50% DCM/trifluoroacetic acid (20 ml) and stirred at RT for 2 h. The solvent was evaporated under reduced pressure and the residue purified by RPHPLC, yield 0.175 g 1H NMR DMSO-d6: δ 8.17-8.16 (1H, s), 7.87-7.84 (1H, d), 7.69-7.61 (2H, m), 7.40 (1H, s), 7.08-7.06 (1H, d), 3.28 (3H, s), 2.87-2.82 (2H, t), 2.62-2.57 (2H, t).

MS: ESI (–ve) 421 (M–1)

EXAMPLE 4

3-[2-[2-Chloro-4-(ethylsulfonyl)phenoxy]-4-(trifluoromethyl)phenyl]propanoic acid

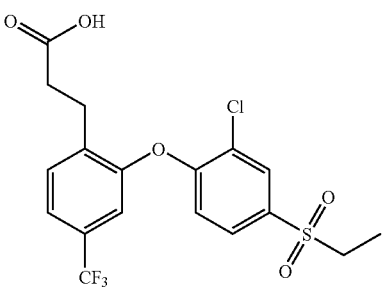

(i) 3-Chloro-4-fluorophenyl ethyl sulfone

The subtitle compound was prepared by the method of example 3 steps (vi)-(vii) using iodoethane.
1H NMR CDCl$_3$: δ 8.01-7.98 (1H, d), 7.84-7.79 (1H, m), 7.37-7.31 (1H, m), 3.17-3.09 (2H, q), 1.33-1.26 (3H, t).

(ii) 3-[2-[2-Chloro-4-(ethylsulfonyl)phenoxy]-4-(trifluoromethyl)phenyl]propanoic acid The title compound was prepared by the method of example 3 using the product from step (i).
1H NMR DMSO-d6: δ 8.07-8.00 (1H, d), 7.81-7.77 (1H, d), 7.698-7.56 (2H, m), 7.40 (1H, bm), 7.01-6.98 (1H, d), 3.39-3.32 (2H, q), 2.77-2.72 (2H, t), 2.26-2.21 (2H, t), 1.14-1.09 (3H, t).
MS: ESI (−ve) 435 (M−1)

EXAMPLE 5

[(4-Chloro-2-{[2-chloro-4-(ethylsulfonyl)phenyl]thio}phenyl)thio]acetic acid

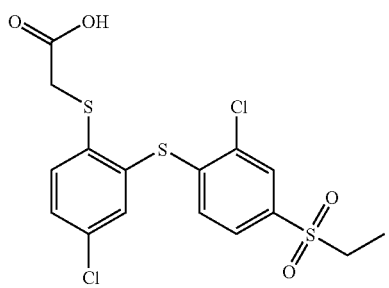

(i) 2-Chloro-4-(ethylsulfonyl)benzenethiol

Sodium hydrosulphide (0.252 g) was added to the product from example 4 step (i) (11.0 g) in dry DMF (10 ml) and stirred at RT for 2 h. The mixture was diluted with 2M sodium hydroxide solution and extracted with diethylether. The aqueous layer was acidified with 2M hydrochloric acid, extracted with ethyl acetate, dried and evaporated under reduced pressure, crude yield 1.60 g.
MS: ESI (−ve) 235 (M−1)

(ii) 4-Chloro-2-{[2-chloro-4-(ethylsulfonyl)phenyl]thio}-1-nitrobenzene

A mixture of the product from step (i) (1.60 g), potassium carbonate (0.934 g) and 2-fluoro-4-chloro-nitrobenzene (1.18 g) in DMF (20 ml) was stirred at RT overnight. Water (200 ml) was added and the mixture extracted with ethyl acetate. The organics were dried, evaporated under reduced and the residue purified by chromatography on silica eluting with isohexane/diethylether 4:1, yield 0.80 g.
1H NMR CDCl$_3$: δ 8.23-8.21 (1H, d), 8.11-8.10 (1H, s), 7.90-7.84 (2H, m), 7.34-7.31 (1H, d), 6.76-6.75 (1H, d), 3.10 (2H, q), 1.37-1.26 (3H, t).

(iii) 4-Chloro-2-{[2-chloro-4-(ethylsulfonyl)phenyl]thio}aniline

The product from step (ii) (0.80 g) and reduced iron powder (0.80 g) in glacial acetic acid (30 ml) was vigorously stirred at RT for 2 h. The mixture was filtered through celite, and the filtrate evaporated under reduced pressure to give a brown oil which was neutralised with 2M NaOH and extracted with ethyl acetate. The organics were dried, evaporated under reduced pressure and the residue purified by chromatography on silica eluting with isohexane/ethylacetate 2:1, yield 0.70 g.
1H NMR CDCl$_3$: δ 7.88-7.87 (1H, m), 7.58-7.54 (1H, m), 7.44-7.43 (1H, m), 7.33-7.28 (1H, m), 6.82-6.75 (2H, m), 4.30 (2H, s), 3.12-3.05 (2H, q), 1.32-1.18 (3H, t).
MS: ESI (−ve) 360 (M−1)

(iv) Ethyl [(4-chloro-2-{[2-chloro-4-(ethylsulfonyl)phenyl]thio}phenyl)thio]acetate Ethyl mercaptoacetate (0.11 ml) followed by isoamylnitrite (0.16 ml) were added to a solution of the product from step (iii) (0.35 g) in dry acetonitrile (20 ml) and heated at 60° C. for 10 h. The mixture was diluted with water, extracted with diethylether, the organics dried and evaporated under reduced pressure. The residue was purified by chromatography on silica eluting with isohexane/diethylether 1:1, yield 0.10 g.
MS: ESI (+ve) 465 (M+1)

(v) [(4-Chloro-2-{[2-chloro-4-(ethylsulfonyl)phenyl]thio}phenyl)thio]acetic acid A mixture of the product from step (iv) (0.10 g), sodium hydroxide (0.018 g) in methanol (5 ml) and water (5 ml) was stirred at RT for 1 h. The mixture was partitioned between 2M hydrochloric acid/ethyl acetate, the organics separated, dried and evaporated under reduced pressure. The residue was purified by reverse phase HPLC. Yield 0.012 g
1H NMR DMSO-d6: δ 7.97 (1H, s), 7.71-7.63 (3H, m), 7.50-7.48 (1H, d), 6.81-6.79 (1H, d), 3.80 (2H, s), 3.40-3.31 (2H, q), 1.11-1.07 (3H, t).
MS: ESI (−ve) 435/437 (M−1)

EXAMPLE 6

N-{4-Chloro-2-[2-chloro-4-(ethylsulfonyl)phenoxy]phenyl}glycine

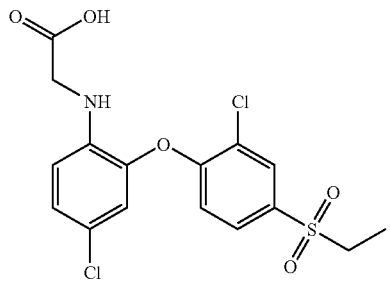

(i) 2-Chloro-4-(ethylsulfonyl)phenol

The product from example 4 step (i) (1.0 g) in dry NMP (20 ml) was treated with 2-butyn-1-ol (0.63 ml) and sodium tert-butoxide (0.864 g) and the mixture stirred at 80° C. for 2 h. The mixture was partitioned between water/ethyl acetate, the organics separated, dried and evaporated under reduced pressure, yield 1.06 g.
MS: ESI (−ve) 219 (M−1)

(ii) 4-Chloro-2-[2-chloro-4-(ethylsulfonyl)phenoxy]-1-nitrobenzene

The subtitle compound was prepared by the method of example 5 step (ii) using the product from step (i). Yield 1.0 g.
1H NMR CDCl₃: δ 8.08-8.05 (2H, m), 7.82-7.78 (1H, d), 7.38-7.26 (1H, d), 7.08-7.04 (2H, d), 3.19-3.12 (2H, q), 1.35-1.30 (3H, t).

(iii) 4-Chloro-2-[2-chloro-4-(ethylsulfonyl)phenoxy]aniline

The subtitle compound was prepared by the method of example 5 step (iii) using the product from step (ii). Yield 0.95 g.
MS: ESI (−ve) 344/346 (M−1)

(iv) Ethyl N-{4-chloro-2-[2-chloro-4-(ethylsulfonyl)phenoxy]phenyl}glycinate A mixture of the product from step (iii) (0.95 g), ethyl bromoacetate (0.145 ml) and sodium acetate (0.160 g) in dry ethanol (30 ml) was heated under reflux 24 h. A further 5 equivalents of ethyl bromoacetate were added and heated for a further 48 h. The mixture was partitioned between water/ethyl acetate, the organics separated, dried and evaporated under reduced pressure. The residue was purified by chromatography on silica eluting with isohexane/diethylether 1:1, yield 0.44 g.
MS: ESI (+ve) 431 (M+1)

(v) N-{4-Chloro-2-[2-chloro-4-(ethylsulfonyl)phenoxy]phenyl}glycine

The title compound was prepared by the method of example 5 step (v) using the product from step (iv). yield 0.181 g.
1H NMR DMSO-d6: δ 8.04 (1H, s), 7.78-7.75 (1H, d), 7.15-7.13 (1H, d), 7.05 (1H, s), 6.98-6.96 (1H, d), 6.65-6.63 (1H, d), 5.40 (1H, bs), 3.40-3.31 (4H, m), 1.13-1.07 (3H, t).
MS: ESI (−ve) 402/404 (M−1)

EXAMPLE 7

({4-Chloro-2-[2-chloro-4-(ethylsulfonyl)phenoxy]phenyl}thio)acetic acid

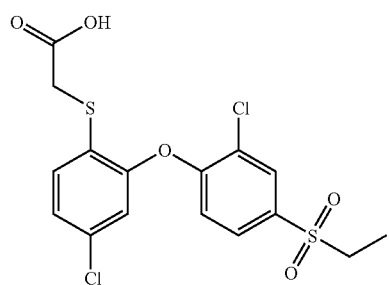

(i) Ethyl ({4-chloro-2-[2-chloro-4-(ethylsulfonyl)phenoxy]phenyl}thio)acetate The subtitle compound was prepared by the method of example 5 step (iv) using the product from example 6 step (iii). Yield 0.4 g.
MS: ESI (+ve) 467 (M+NH4)

(ii) ({4-Chloro-2-[2-chloro-4-(ethylsulfonyl)phenoxy]phenyl}thio)acetic acid The title compound was prepared by the method of example 5 step (v) using the product from step (i), yield 0.02 g.
1H NMR DMSO-d6: δ 8.07 (1H, s), 7.79-7.76 (1H, d), 7.54-7.47 (1H, d), 7.41-7.33 (2H, m), 7.00-6.97 (1H, d), 3.77 (2H, s), 3.50-3.23 (2H, q), 1.23-1.05 (3H, t).
MS: ESI (−ve) 419/421 (M−1)

EXAMPLE 8

3-{2-[2-Chloro-4-(methylsulfonyl)phenoxy]-4-fluorophenyl}propanoic acid

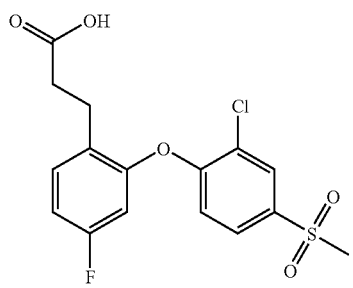

The title compound was prepared by the method of example 3 using 4-fluoro-2-methoxybenzaldehyde, yield 0.137 g.
1H NMR DMSO-d6: δ 8.15-8.14 (1H, s), 7.86-7.83 (1H, d), 7.48-7.44 (1H, m), 7.13-7.07 (2H, m), 6.99-6.96 (1H, d), 3.27 (3H, s), 2.76-2.72 (2H, t), 2.54-2.49 (2H, t).
MS: ESI (−ve) 371 (M−1)

EXAMPLE 9

{2-[2-Chloro-4-(methylsulfonyl)phenoxy]-4-fluorophenyl}acetic acid

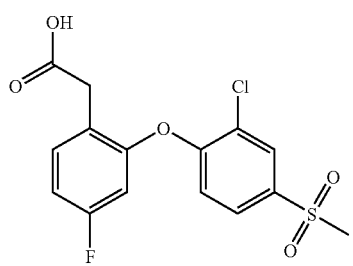

(i) 4-Fluoro-2-hydroxybenzaldehyde

The subtitle compound was prepared by the method of example 3 step (ii) using 4-fluoro-2-methoxybenzaldehyde, yield 3.0 g.
1H NMR CDCl₃: δ 11.83 (1H, s), 9.83 (1H, s), 7.58-7.53 (1H, m), 6.75-6.65 (2H, m).

(ii) 2-(Benzyloxy)-4-fluorobenzaldehyde

A mixture of the product from step (i) (3.0 g), potassium carbonate (4.42 g) and benzyl bromide (3.90 ml) in DMF (40 ml) was heated at 90° C. for 14 h. The mixture was partitioned between water/ethyl acetate, the organics separated, dried and evaporated under reduced pressure. The residue was purified by chromatography on silica eluting with isohexane/diethyl-ether 5:1, yield 6.3 g.

(iii) [2-(Benzyloxy)-4-fluorophenyl]methanol

Sodium borohydride (0.223 g) was added to a solution of the product from step (ii) (1.07 g) in dry ethanol (30 ml) and the mixture was stirred at RT overnight. The mixture was partitioned between 2M hydrochloric acid/ethyl acetate, the organics separated, dried and evaporated under reduced pressure, yield 1.08 g.

MS: ESI (−ve) 231 (M−1)

(iv) Benzyl 2-(chloromethyl)-5-fluorophenyl ether

A mixture of the product from step (iii) (1.06 g), methane sulphonyl chloride (0.351 ml) and triethylamine (0.636 ml) in DCM (20 ml) was stirred at RT for 2 h. The mixture was partitioned between water/DCM, the organics separated, dried and evaporated under reduced pressure. The residue was purified by chromatography on silica eluting with iso-hexane/DCM 1:1, yield 0.7 g.

1H NMR CDCl$_3$: δ 7.47-7.25 (6H, m), 6.69-6.62 (2H, m), 5.11 (2H, s), 4.59 (2H, s).

(v) [2-(Benzyloxy)-4-fluorophenyl]acetic acid

A mixture of the product from step (iv) (0.7 g) and sodium cyanide (0.162 g) in DMSO (20 ml) was heated at 60° C. for 2 h. 2M Sodium hydroxide (10 ml) was added and the mixture heated at 100° C. for 6 h then stirred at RT for 2 h. The mixture was partitioned between 2M hydrochloric acid/ethyl acetate, the organics separated, dried and evaporated under reduced pressure, yield 0.68 g.

MS: ESI (−ve) 259 (M−1)

(vi) (4-Fluoro-2-hydroxyphenyl)acetic acid

The subtitle compound was prepared by the method of example 3 step (v), yield 0.34 g.

MS: ESI (−ve) 169 (M−1)

(vii) {2-[2-Chloro-4-(methylsulfonyl)phenoxy]-4-fluorophenyl}acetic acid

Sodium hydride (60% wt. disp. oil, 0.176 g) was added to a solution of the product from step (vi) (0.34 g) in dry DMF (10 ml) and stirred at RT for 1 h before adding the product from example 3 step (vii) (0.416 g). The mixture was heated at 80° C. for 1 h, then partitioned between 2M hydrochloric acid/ethyl acetate. The organics were dried, evaporated under reduced pressure and the residue purified by reverse phase HPLC. Yield 0.064 g 1H NMR DMSO-d6: δ 8.10 (1H, s), 7.82-7.80 (1H, d), 7.48-7.44 (1H, m), 7.11-7.08 (2H, m), 6.97-6.94 (1H, d), 3.41-3.35 (2H, s), 3.26 (3H, s).

MS: ESI (−ve) 357 (M−1)

EXAMPLE 10

4-chloro-2-[2-chloro-4-(methylsulfonyl)phenoxy]-α-methyl-benzenepropanoic acid

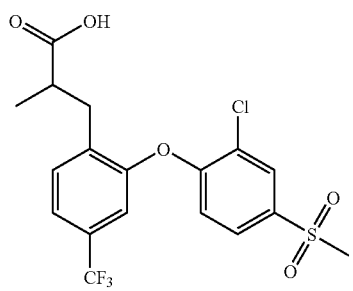

i) (2E)-3-(4-chloro-2-methoxyphenyl)-2-methyl-, ethyl ester, 2-propenoic acid

The subtitle compound was prepared by the method of example 3 step iv) using ethyl-P,P-dimethylphosphonoac-etate with the product from example 3 step i) Yield 1.85 g.

1H NMR CDCl$_3$: δ 7.75-7.10 (4H, m), 4.31-4.25 (2H, q), 3.90 (3H, s), 2.03-2.02 (3H, s), 1.37-1.33 (3H, t).

ii) (2E)-3-(4-chloro-2-hydroxyphenyl)-2-methyl-2-propenoic acid, ethyl ester

The subtitle compound was prepared by the method of example 3 step ii) using the product from step i) Yield 1.80 g.

MS: ESI (−ve) 273 (M−1)

iii) (2E)-3-[4-chloro-2-[2-chloro-4-(methylsulfonyl) phenoxy]phenyl]-2-methyl-2-propenoic acid The subtitle compound was prepared by the method of example 3 step viii) using the product from step ii) Yield 0.35 g.

1H NMR DMSO-d6: δ 12.74 (1H, bs), (1H, m), 7.49 (6H, m), 7.12-7.10 (1H, d), 3.27-3.26 (3H, s), 1.94 (3H, s).

iv) 4-chloro-2-[2-chloro-4-(methylsulfonyl)phe-noxy]-α-methyl-benzenepropanoic acid The title compound was prepared by the method of example 3 step v) using the product from step iii).

1H NMR DMSO-d6: δ 8.10 (1H, s), 7.82-7.80 (1H, d), 7.48-7.44 (1H, m), 7.11-7.08 (2H, m), 6.97-6.94 (1H, d), 3.41-3.35 (2H, s), 3.26 (3H, s).

MS: ESI (−ve) 435 (M−1)

EXAMPLE 11

N-[2-[2-chloro-4-(methylsulfonyl)phenoxy]-4-fluo-rophenyl]-glycine

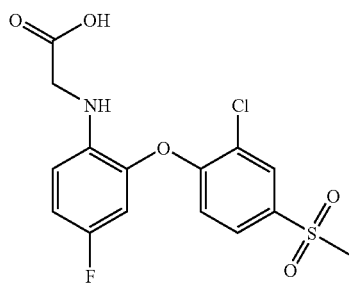

i) 2-amino-5-fluoro-phenol

The subtitle compound was prepared by the method of example 3 step v) using 2-nitro-5-fluoro phenol. Yield 1.74 g.

MS: ESI (−ve) 126 (M−1)

ii) 2-[2-chloro-4-(methylsulfonyl)phenoxy]-4-fluoro-benzenamine

The subtitle compound was prepared by the method of example 3 step viii) using the product from step i). Yield 1.00 g.

1H NMR CDCl₃: δ 8.05-7.73 (2H, m), 6.95-6.67 (4H, m), 3.48-3.47 (2H, bs), 3.06 (3H, s).

MS: ESI (−ve) 314 (M−1)

iii) N-[2-[2-chloro-4-(methylsulfonyl)phenoxy]-4-fluorophenyl]-glycine

The title compound was prepared by the methods of example 6 step iv-v) using the product from step ii).

1H NMR DMSO-d6: δ 8.10-6.62 (6H, m), 5.20 (1H, bs), 3.47 (2H, s), 3.25 (3H, s).

MS: ESI (−ve) 372 (M−1)

EXAMPLE 12

N-[2-[2-chloro-4-(ethylsulfonyl)phenoxy]-4-fluorophenyl]-glycine

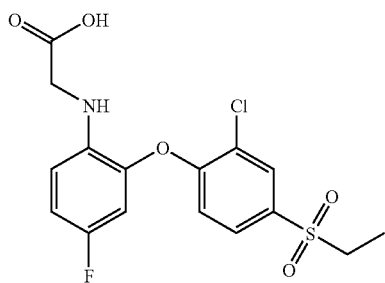

i) 2-[2-chloro-4-(ethylsulfonyl)phenoxy]-4-fluoro-benzenamine

The subtitle compound was prepared by the method of example 11 step ii) using the product from example 4 step i) Yield 0.7 g.

MS: ESI (+ve) 330 (M+1)

ii) N-[2-[2-chloro-4-(ethylsulfonyl)phenoxy]-4-fluorophenyl]-glycine

The title compound was prepared by the method of example 6 step iv) using the product from step i).

1H NMR DMSO-d6: δ 8.04-8.02 (1 h, s), 7.78-7.74 (1H, d), 7.02-6.86 (3H, m), 6.69-6.65 (1H, m), (2H, m), 3.72 (2H, s), 3.41-3.30 (2H, q), 1.13-1.06 (3H, t).

MS: ESI (−ve) 386 (M−1)

EXAMPLE 13

N-[2-[2-chloro-4-(methylsulfonyl)phenoxy]-4-fluorophenyl]-2-methyl-alanine

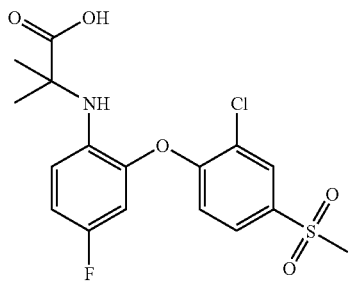

The title compound was prepared using the product from example 11 step ii) (0.50 g) which was dissolved in dry acetone (30 ml) and treated with trichloro-methylpropanol (0.75 g). The mixture was cooled to 0 C before adding crushed sodium hydroxide (0.183 g) and stirring for 1 hour at room temperature. This process was repeated a further two times and left to stir at room temperature overnight. The mixture was extracted with ether (discarded). The aqueous layer was acidified and extracted with ethyl acetate, dried and concentrated under reduced pressure to an oil. The residue was purified by reverse phase HPLC to give a white solid.

1H NMR DMSO-d6: δ 8.11-8.10 (1h, s), 7.84-7.80 (1H, d), 7.01-6.89 (3H, m), 6.72-6.67 (1H, m), 3.31 (3H, s), 1.41 (6H, s).

MS: ESI (−ve) 400 (M−1)

EXAMPLE 14

N-[2-[2-chloro-4-(methylsulfonyl)phenoxy]-4-fluorophenyl]-D-alanine

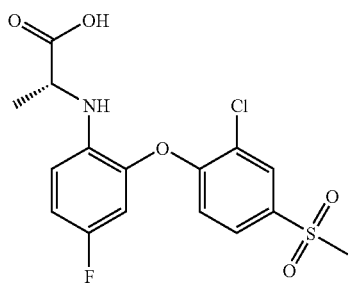

i) N-[2-[2-chloro-4-(methylsulfonyl)phenoxy]-4-fluorophenyl]-D-alanine, ethyl ester The subtitle compound was prepared using the product from example 11 step ii) (0.44 g) which was dissolved in dry DCM (20 ml) and treated with 2,6-lutidine (0.162 ml) followed by ethyl-o-trifluoromethanesulphonyl-D-lactate (0.285 ml). The mixture was stirred at room temperature overnight. The mixture was concentrated under reduced pressure to an oil. The residue was purified by chromatography eluting with ether/isohexane 1:1, yield 0.6 g.

MS: ESI (−ve) 414 (M−1)

ii) N-[2-[2-chloro-4-(methylsulfonyl)phenoxy]-4-fluorophenyl]-D-alanine

The title compound was prepared using the method of example 5 step v) using the product from step i).
1H NMR DMSO-d6: δ 8.11-8.10 (1H, s), 7.83-7.79 (1H, d), 7.03-6.74 (4H, m), 4.14-4.07 (1H, q), 3.26 (3H, s), 1.35-1.26 (3H, d).
MS: ESI (−ve) 386 (M−1)

EXAMPLE 15

N-[4-chloro-2-[2-chloro-4-(methylsulfonyl)phenoxy]phenyl]-glycine

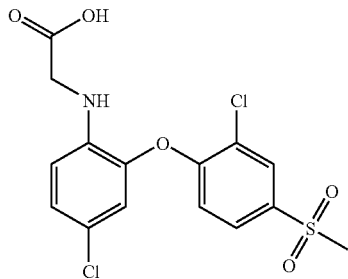

i) 4-chloro-2-[2-chloro-4-(methylsulfonyl)phenoxy]-benzenamine

The subtitle compound was prepared by the method of example 3 step viii) using 4-chloro-2-hydroxyaniline and the product from example 3 step vii). Yield 3.0 g.
MS: ESI (−ve) 330 (M−1)

ii) N-[4-chloro-2-[2-chloro-4-(methylsulfonyl)phenoxy]phenyl]-glycine, ethyl ester The subtitle compound was prepared by the method of example 6 step iv) using the product from step i). Yield 0.6 g.
MS: ESI (+ve) 418 (M+1)

iii) N-[4-chloro-2-[2-chloro-4-(methylsulfonyl)phenoxy]phenyl]-glycine

The title compound was prepared by the method of example 5 step v) using the product from step ii).
1H NMR DMSO-d6: δ 8.11-8.10 (1H, s), 7.82-7.79 (1H, d), 7.16-6.94 (3H, m), 6.67-6.64 (1H, d), 5.49 (1H, m), 3.51 (2H, s), 3.25 (3H, s).
MS: ESI (−ve) 388 (M−1)

EXAMPLE 16

[[4-chloro-2-[2-chloro-4-(methylsulfonyl)phenoxy]phenyl]thio]-acetic acid

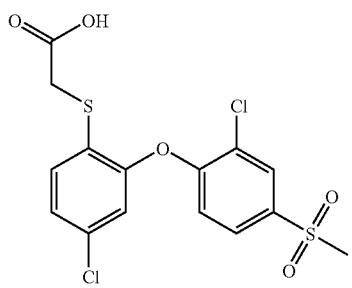

i) [[4-chloro-2-[2-chloro-4-(methylsulfonyl)phenoxy]phenyl]thio]-acetic acid, ethyl ester Ethyl mercaptoacetate (0.11 ml) followed by isoamylnitrite (0.16 ml) were added to a solution of the product from example 15 step (i) (0.5 g) in dry acetonitrile (20 ml) and heated at 60° C. for 10 h. The mixture was diluted with water, extracted with diethylether, the organics dried and evaporated under reduced pressure. The residue was purified by chromatography on silica eluting with dichloromethane, yield 0.60 g.
MS: ESI (+ve) 435 (M+1)

ii) [[4-chloro-2-[2-chloro-4-(methylsulfonyl)phenoxy]phenyl]thio]-acetic acid

The title compound was prepared by the method of example 5 step v) using the product from step i).
1H NMR DMSO-d6: δ 8.13-8.12 (1H, s), 7.84-7.80 (1H, d), 7.50-7.29 (3H, m), 6.99-6.96 (1H, d), 3.75 (2H, s), 3.27 (3H, s).
MS: ESI (−ve) 405 (M−1)

EXAMPLE 17

N-[2-[2-chloro-4-(ethylsulfonyl)phenoxy]-4-fluorophenyl]-D-alanine

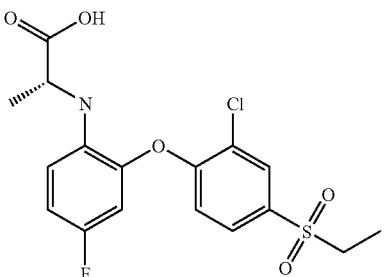

i) N-[2-[2-chloro-4-(ethylsulfonyl)phenoxy]-4-fluorophenyl]-D-alanine, methyl ester The subtitle compound was prepared by the method of example 14 step i) using the product from example 15 step i). Yield 0.5 g.
MS: ESI (−ve) 416 (M−1)

ii) N-[2-[2-chloro-4-(ethylsulfonyl)phenoxy]-4-fluorophenyl]-D-alanine

The title compound was prepared by the method of example 5 step v) using the product from step i).
1H NMR DMSO-d6: δ 8.04-8.03 (1H, s), 7.77-7.75 (1H, d), 6.98-6.91 (3H, m), 6.69-6.65 (1H, m), 5.40 (1H, m), 3.52-3.50 (1H, q), 3.40-3.30 (2H, q), 1.20-1.18 (3H, d), 1.13-1.07 (3H, t).
MS: ESI (−ve) 400 (M−1)

EXAMPLE 18

N-[4-chloro-2-[2-chloro-4-(methylsulfonyl)phenoxy]phenyl]-D-alanine

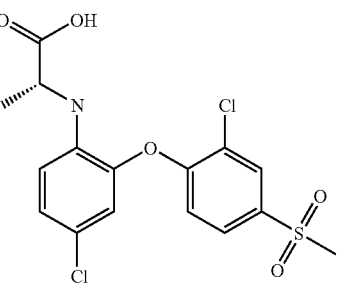

i) N-[4-chloro-2-[2-chloro-4-(methylsulfonyl)phenoxy]phenyl]-D-alanine, methyl ester The subtitle compound was prepared by the method of example 14 step i) using the product from example 12 step i). Yield 0.6 g.

MS: ESI (+ve) 418 (M+1)

ii) N-[4-chloro-2-[2-chloro-4-(methylsulfonyl)phenoxy]phenyl]-D-alanine

The title compound was prepared by the method of example 5 step v) using the product from step i).

1H NMR DMSO-d6: δ 8.11-8.10 (1H, s), 7.83-7.80 (1H, d), 7.16-7.14 (1H, d), 7.01-6.97 (2H, m), 6.77-6.74 (1H, d), 5.40 (1H, m), 4.13-4.11 (1H, q), 3.40-3.30 (3H, s), 1.36-1.35 (3H, d).

MS: ESI (−ve) 402 (M−1)

EXAMPLE 19

N-[4-chloro-2-[2-chloro-4-(methylsulfonyl)phenoxy]phenyl]-N-methyl-glycine

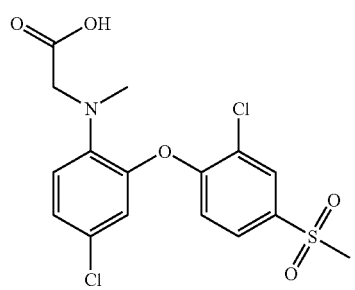

i) N-[4-chloro-2-[2-chloro-4-(methylsulfonyl)phenoxy]phenyl]-N-methyl-glycine, ethyl ester The subtitle compound was prepared by using the product from example 15 step ii). (0.70 g) which was dissolved in dimethylsulphate (3 ml). Sodium hydrogen carbonate (0.355 g) was added and heated to 90 C for 2 hours. The mixture was diluted with water, extracted with ethyl acetate, dried, and concentrated under reduced pressure to give an oil. The residue was purified by chromatography on silica eluting with diethyl ether, yield 0.70 g.

MS: ESI (+ve) 432 (M+1)

ii) N-[4-chloro-2-[2-chloro-4-(methylsulfonyl)phenoxy]phenyl]-N-methyl-glycine

The title compound was prepared by the method of example 5 step v) using the product from step i).

1H NMR DMSO-d6: δ 8.07 (1H, s), 7.77-7.74 (1H, d), 7.22-7.02 (3H, m), 6.82-6.80 (1H, d), 3.69 (2H, s), 3.24 (3H, s), 2.80 (3H, s).

MS: ESI (−ve) 402 (M−1)

EXAMPLE 20

2-[2-chloro-4-(ethylsulfonyl)phenoxy]-4-fluoro-benzenepropanoic acid

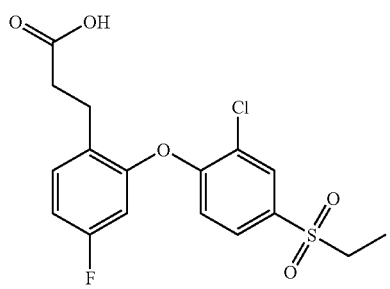

i) 4-fluoro-2-hydroxy-benzenepropanoic acid

The subtitle compound was prepared by the method of example 3 steps ii-v) using 4-fluoro-2-methoxybenzaldehyde, yield 1.90 g.

MS: ESI (−ve) 211 (M−1)

ii) 2-[2-chloro-4-(ethylsulfonyl)phenoxy]-4-fluoro-benzenepropanoic acid, ethyl ester The subtitle compound was prepared by the method of example 3 step viii) using the product from step i) and the product from example 4 step i) yield (0.45 g).

MS: ESI (+ve) 432 (M+NH4)

iii) 2-[2-chloro-4-(ethylsulfonyl)phenoxy]-4-fluoro-benzenepropanoic acid

The title compound was prepared by the method of example 5 step v) using the product from step ii).

1H NMR DMSO-d6: δ 8.05-8.04 (1H, s), 7.79-7.76 (1H, m), 7.47-7.43 (1H, m), 7.08-6.96 (3H, m), 3.37-3.35 (2H, q), 2.63-2.59 (2H, t), 2.07-2.03 (2H, t), 1.13-1.10 (3H, t).

MS: ESI (−ve) 385 (M−1)

EXAMPLE 21

2-[4-(ethylsulfonyl)-3-(trifluoromethyl)phenoxy]-4-fluoro-benzenepropanoic acid

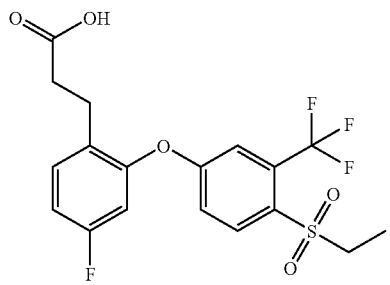

i) 2-[4-(ethylsulfonyl)-3-(trifluoromethyl)phenoxy]-4-fluoro-benzenepropanoic acid, ethyl ester The subtitle compound was prepared by the method of example 3 step viii) using 4-bromo-1-(methylsulphonyl)-2-trifluoromethylbenzene yield and the product from example 20 step i) 0.60 g.

MS: ESI (+ve) 452 (M+NH4)

ii) 2-[4-(ethylsulfonyl)-3-(trifluoromethyl)phenoxy]-4-fluoro-benzenepropanoic acid The title compound was prepared by the method of example 5 step v) using the product from step i).

1H NMR DMSO-d6: δ 8.20-8.17 (1H, d), 7.54-7.45 (2H, m), 7.28-7.25 (1H, d), 7.12-7.05 (2H, m), 3.27 (3H, s), 2.62-2.55 (2H, t), 2.05-1.99 (3H, t).

MS: ESI (−ve) 405 (M−1)

EXAMPLE 22

2-[4-(ethylsulfonyl)-3-(trifluoromethyl)phenoxy]-4-fluoro-benzenepropanoic acid

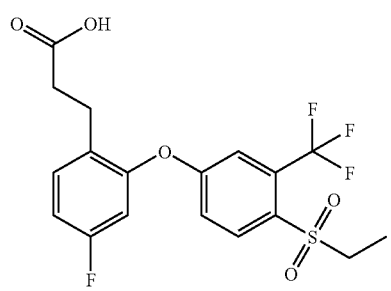

i) 4-bromo-1-(ethylsulfonyl)-2-(trifluoromethyl)-benzene

The subtitle compound was prepared by the method of example 3 step vii) using 4-bromo-1-(ethylthio)-2-trifluoromethylbenzene yield (0.97 g).

1H NMR CDCl3: δ 8.13-7.89 (3H, m), 3.31-3.24 (2H, q), 1.34-1.29 (3H, t).

ii) 3-{2-[4-(ethylsulfonyl)-3-(trifluoromethyl)phenoxy]-4-fluorophenyl}propanoic acid The title compound was prepared by the method of example 21 using the product from step i).

1H NMR DMSO-d6: δ 8.20-8.17 (1H, d), 7.54-7.45 (2H, m), 7.28-7.25 (1H, d), 7.07-7.02 (2H, m), 3.35-3.32 (2H, q), 2.60-2.54 (2H, t), 2.04-2.00 (2H, t), 1.17-1.14 (3H, t).

MS: ESI (−ve) 405 (M−1)

EXAMPLE 23

N-[4-chloro-2-[[4-(ethylsulfonyl)phenyl]thio]phenyl]-glycine

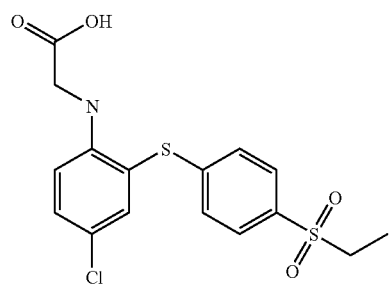

i) N-[4-chloro-2-[[4-(ethylsulfonyl)phenyl]thio]phenyl]-glycine, ethyl ester

The subtitle compound was prepared by the method of example 6 step iv) using the product from example 5 step iii) yield 0.30 g.

MS: ESI (+ve) 448 (M+H)

ii) N-[4-chloro-2-[[4-(ethylsulfonyl)phenyl]thio]phenyl]-glycine

The title compound was prepared by the method of example 5 step v) using the product from step i).

1H NMR DMSO-d6: δ 12.65 (1H, s), 7.936-7.93 (1H, s), 7.66-7.41 (3H, m), 6.80-6.71 (2H, m), 6.06-6.02 (1H, t), 3.90-3.88 (2H, d), 3.39-3.35 (2H, q), 1.10-1.05 (3H, t).

MS: ESI (−ve) 418 (M−1)

EXAMPLE 24

N-[4-chloro-2-[[4-(ethylsulfonyl)phenyl]thio]phenyl]-D-alanine

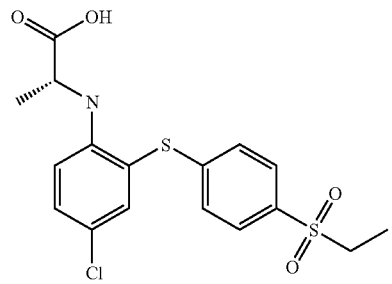

The title compound was prepared by the method of example 14 steps i-ii) using the product from example 5 step iii).

1H NMR DMSO-d6: δ 7.94-7.93 (1H, s), 7.68-7.64 (1H, d), 7.51-7.42 (2H, m), 6.80-6.75 (2H, m), 5.78-5.76 (1H, d), 4.07-4.05 (1H, q), 3.41-3.27 (2H, q), 1.27-1.24 (3H, d), 1.16-1.05 (3H, t).

MS: ESI (−ve) 432 (M−1)

EXAMPLE 25

N-[4-chloro-2-[4-(ethylsulfonyl)-3-(trifluoromethyl)phenoxy]phenyl]-glycine i) 4-chloro-2-[4-(ethylsulfonyl)-3-(trifluoromethyl)phenoxy]-benzenamine

The subtitle compound was prepared by the example 3 step viii) using the product from example 22 step i) and 2-amino-5-chlorophenol. Yield 11.0 g
MS: ESI (−ve) 378 (M−1)

ii) N-[4-chloro-2-[4-(ethylsulfonyl)-3-(trifluoromethyl)phenoxy]phenyl]-glycine The title compound was prepared by the method of example 15 steps ii-iii) using the product from step i).
1H NMR DMSO-d6: δ 8.14-8.11 (1H, d), 7.58-7.57 (1H, m), 7.29-7.14 (3H, m), 6.69-6.66 (1H, d), 5.67 (1H, m), 3.61 (2H, s), 3.39-3.28 (2H, q), 1.23-1.15 (3H, t).
MS: ESI (−ve) 436 (M−1)

EXAMPLE 26

N-[4-chloro-2-[4-(ethylsulfonyl)-3-(trifluoromethyl)phenoxy]phenyl]-D-alanine

The title compound was prepared by the method of example 14 steps i-ii) using the product from example 25 step i).
1H NMR DMSO-d6: δ 8.14-8.11 (1H, d), 7.589-7.58 (1H, m), 7.29-7.16 (3H, m), 6.76-6.73 (1H, d), 5.62 (1H, m), 4.11-4.09 (1H, m), 3.36-3.28 (2H, q), 1.34-1.32 (3H, d), 1.18-1.13 (3H, t).
MS: ESI (−ve) 450 (M−1)

EXAMPLE 27

N-[2-[2-chloro-4-(ethylsulfonyl)phenoxy]-4-(trifluoromethyl)phenyl]-glycine i) 2-nitro-5-(trifluoromethyl)-phenol

The subtitle compound was prepared by using 3-(1,1,1-trifluoromethyl)phenol (5.0 g) which was cooled to 0 C and 65% nitric acid (6 ml) was added dropwise. After the addition, the mixture was kept at 0 C for 1 hour. This was diluted with saturated sodium acetate solution, extracted with ethyl acetate, dried and concentrated under reduced pressure to give an oil. Yield 3.67 g
MS: ESI (+ve) 206 (M+1)

ii) 2-amino-5-(trifluoromethyl)-phenol

The subtitle compound was prepared by the method of example 3 step v) using the product from step i) Yield 1.50 g.
MS: ESI (+ve) 186 (M+1)

iii) N-[2-[2-chloro-4-(ethylsulfonyl)phenoxy]-4-(trifluoromethyl)phenyl]-glycine The title compound was prepared by the method of example 12 steps i-ii) using the product from step ii).
1H NMR DMSO-d6: δ 12.84 (1H, bs), 8.027-8.02 (1H, s), 7.78-7.74 (1H, m), 7.34-7.30 (2H, m), 6.97-6.94 (1H, m), 6.78-6.75 (1H, d), 5.78-5.76 (1H, t), 3.98-3.96 (2H, d), 3.36-3.29 (2H, q), 1.16-1.08 (3H, t).
MS: ESI (−ve) 436 (M−1)

EXAMPLE 28

N-[2-[4-(ethylsulfonyl)-3-(trifluoromethyl)phenoxy]-4-(trifluoromethyl)phenyl]-glycine The title compound was prepared by the method of example 25 steps i-ii) using the product from example 27 step ii).

1H NMR DMSO-d6: δ 8.13-8.10 (1H, d), 7.54-7.24 (4H, m), 6.79-6.76 (1H, d), 5.78-5.76 (1H, t), 3.99-3.97 (2H, d), 3.35-3.27 (2H, q), 1.17-1.12 (3H, t).
MS: ESI (−ve) 436 (M−1)

EXAMPLE 29

N-[4-chloro-2-(2-chloro-4-cyanophenoxy)phenyl]-glycine

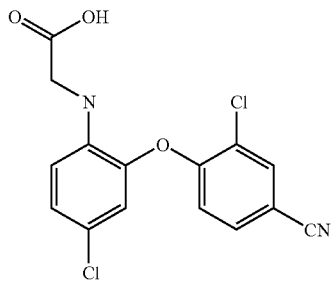

i) 4-(2-amino-5-chlorophenoxy)-3-chloro-benzonitrile

The subtitle compound was prepared by the method of example 3 step viii) using 2-amino-5-chlorophenol and 3-chloro-4-fluorobenzonitrile. Yield 2.70 g
1H NMR CDCl$_3$: δ 7.76-7.75 (1H, s), 7.49-7.46 (1H, d), 7.07-6.77 (4H, m), 3.79 (2H, s).

ii) N-[4-chloro-2-(2-chloro-4-cyanophenoxy)phenyl]-glycine, ethyl ester

The subtitle compound was prepared by the method of example 1 step ii) using the product from step i). Yield 1.65 g.
MS: ESI (−ve) 363 (M−1)

iii) N-[4-chloro-2-(2-chloro-4-cyanophenoxy)phenyl]-glycine

The title compound was prepared by the method of example 5 step v) using the product from step ii).
1H NMR DMSO-d6: δ 8.197-8.19 (1H, s), 7.76-7.73 (1H, d), 7.16-7.13 (1H, d), 7.04-7.03 (1H, s), 6.88-6.85 (1H, d), 6.70-6.67 (1H, d), 5.78-5.70 (1H, m), 3.84 (2H, s).
MS: ESI (−ve) 335 (M−1)

EXAMPLE 30

N-[2-(4-bromo-2-chlorophenoxy)-4-chlorophenyl]-glycine

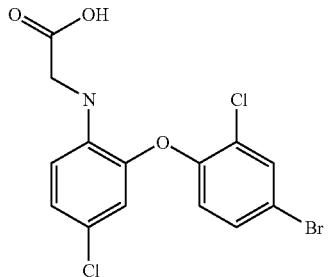

i) 2-(4-bromo-2-chlorophenoxy)-4-chloro-benzenamine

The subtitle compound was prepared by the method of example 3 step viii) using 2-amino-5-chlorophenol and 3-chloro-4-fluorobromobenzene. Yield 2.05 g.
1H NMR CDCl$_3$: δ 7.61-7.60 (1H, s), 7.37-7.25 (1H, m), 7.05-6.93 (1H, m), 6.83-6.71 (3H, m), 3.85 (2H, s).

ii) N-[2-(4-bromo-2-chlorophenoxy)-4-chlorophenyl]-glycine, ethyl ester

The subtitle compound was prepared by the method of example 1 step ii) using the product from step i). Yield 2.50 g.
MS: ESI (+ve) 420 (M+1)

iii) N-[2-(4-bromo-2-chlorophenoxy)-4-chlorophenyl]-glycine

The title compound was prepared by the method of example 5 step v) using the product from step ii).
1H NMR DMSO-d6: δ 7.86-7.85 (1H, s), 7.52-7.48 (1H, d), 7.08-7.04 (1H, d), 6.89-6.86 (1H, d), 6.78-6.77 (1H, s), 6.66-6.63 (1H, d), 5.64 (1H, m), 3.86 (2H, s).
MS: ESI (−ve) 391 (M−1)

EXAMPLE 31

N-[4-chloro-2-[2-chloro-4-(5-methyl-1,2,4-oxadiazol-3-yl)phenoxy]phenyl]-glycine

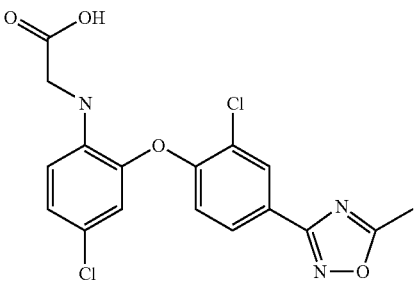

i) 4-(2-amino-5-chlorophenoxy)-3-chloro-N-hydroxy-benzene carboximidamide

The subtitle compound was prepared using the product from example 29 step i) (0.60 g) which was dissolved in ethanol (20 ml) and treated with hydroxylamine hydrochloride (0.30 g) followed by potassium carbonate (0.60 g). The mixture was heated at 90 C for 2 hours, cooled and the solid filtered off. The filtrate was concentrated under reduced pressure to give a red oil. Yield 0.94 g.
MS: ESI (+ve) 312 (M+1)

ii) N-[4-chloro-2-[2-chloro-4-(5-methyl-1,2,4-oxadiazol-3-yl)phenoxy]phenyl]-acetamide The subtitle compound was prepared using the product from step i) (0.94 g) which was dissolved in pyridine (10 ml) and treated with acetyl chloride (0.22 ml) at 0 C. This was then allowed to warm to room temperature. The mixture was heated at reflux for 3 hours, diluted with 2M HCl, extracted with ethyl acetate, dried and concentrated under reduced pressure to an oil. The residue was purified by chromatography on silica eluting with diethyl ether/isohexane 3:1, yield 0.50 g.

1H NMR CDCl₃: δ 8.43-8.40 (1H, d), 8.25-8.23 (1H, s), 8.02-7.97 (1H, d), 7.67-7.56 (1H, bs), 7.21-7.11 (2H, d), 6.81-6.75 (1H, s), 2.68-2.67 (3H, s), 2.21-2.18 (3H, s).

iii) 4-chloro-2-[2-chloro-4-(5-methyl-1,2,4-oxadiazol-3-yl)phenoxy]-benzenamine

The subtitle compound was prepared using the product from step ii) (0.50 g) which was dissolved in 2M HCl (10 ml) and ethanol (10 ml). The mixture was heated at reflux for 3 hours and concentrated under reduced pressure to an solid. Yield 0.45 g.

MS: ESI (+ve) 335 (M+1)

iv) N-[4-chloro-2-[2-chloro-4-(5-methyl-1,2,4-oxadiazol-3-yl)phenoxy]phenyl]-glycine The title compound was prepared by the method of example 6 steps iv-v) using the product from step iii).

1H NMR DMSO-d6: δ 8.09 (1H, s), 7.92-7.89 (1H, d), 7.14-7.10 (1H, d), 7.01-6.95 (2H, m), 6.70-6.67 (1H, d), 5.67 (1H, bs), 3.87 (2H, s), 2.66 (3H, s).

MS: ESI (-ve) 392 (M-1)

EXAMPLE 32

N-[4-chloro-2-[2-chloro-4-(5-ethyl-1,2,4-oxadiazol-3-yl)phenoxy]phenyl]-glycine

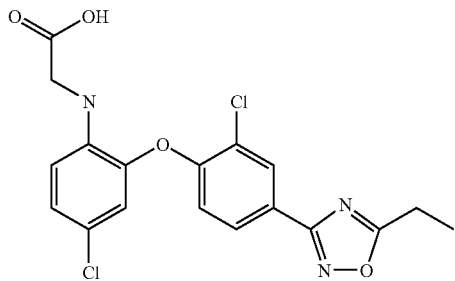

i) N-[4-chloro-2-[2-chloro-4-[(hydroxyamino)iminomethyl]phenoxy]phenyl]-glycine, ethyl ester The subtitle compound was prepared by the method of example 31 step i) using the product from example 29 step ii). Yield 0.60 g.

MS: ESI (+ve) 398 (M+1)

ii) N-[4-chloro-2-[2-chloro-4-(5-ethyl-1,2,4-oxadiazol-3-yl)phenoxy]phenyl]-glycine, ethyl ester The subtitle compound was prepared by the method of example 31 step ii) using the product from step i). Yield 0.60 g.

MS: ESI (+ve) 436 (M+1)

iii) N-[4-chloro-2-[2-chloro-4-(5-ethyl-1,2,4-oxadiazol-3-yl)phenoxy]phenyl]-glycine The title compound was prepared by the method of example 5 step v) using the product from step ii).

1H NMR DMSO-d6: δ 8.10 (1H, s), 7.93-7.89 (1H, d), 7.14-7.10 (1H, d), 7.01-6.95 (2H, m), 6.70-6.67 (1H, d), 5.68 (1H, bm), 3.87 (2H, s), 3.05-2.98 (2H, q), 1.26-1.24 (3H, t).

MS: ESI (-ve) 408 (M-1)

EXAMPLE 33

N-[4-chloro-2-[2-chloro-4-(5-pyrimidinyl)phenoxy]phenyl]-glycine

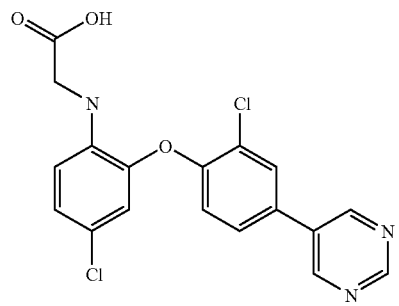

i) N-[4-chloro-2-[2-chloro-4-(5-pyrimidinyl)phenoxy]phenyl]-glycine, ethyl ester The subtitle compound was prepared by using the product from example 30 step ii) (0.20 g) which was dissolved in dry dioxane (10 ml). Cesium fluoride (0.15 g) followed by pyrimidine-5-boronic acid (0.058 g) and Palladium(diphenylphosphinoferrocene) dichloride (0.017 g) were added and the mixture was heated at 80 C for 10 hours. The mixture was diluted with 2M HCl, extracted with ethyl acetate, dried and concentrated under reduced pressure to give an oil. Yield 0.20 g.

MS: ESI (+ve) 417 (M+1)

ii) N-[4-chloro-2-[2-chloro-4-(5-pyrimidinyl)phenoxy]phenyl]-glycine

The title compound was prepared by the method of example 5 step v) using the product from step i).

1H NMR DMSO-d6: δ 9.19-9.17 (3H, m), 8.12-8.11 (1H, m), 7.79-7.75 (1H, m), 7.10-7.04 (2H, m), 6.80-6.79 (1H, m), 6.68-6.65 (1H, d), 5.70 (1H, bm), 3.89 (2H, s).

MS: ESI (-ve) 388 (M-1)

EXAMPLE 34

N-[4-chloro-2-[2-chloro-4-(2-pyridinyl)phenoxy]phenyl]-glycine

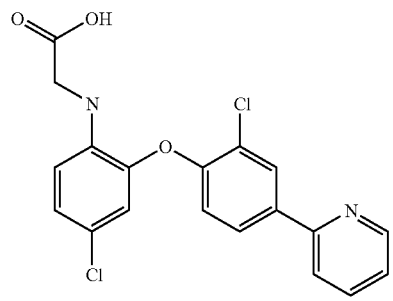

i) N-[4-chloro-2-[2-chloro-4-(2-pyridinyl)phenoxy]phenyl]-glycine, ethyl ester

The subtitle compound was prepared by using the product from example 30 step ii) (0.20 g) which was dissolved in dry dioxane (10 ml). 2-pyridyl tributyl tin (0.181 g) and palladium (0) tetrakistriphenylphosphine (0.028 g) were added and the mixture was heated at 80 C for 16 hours. The mixture was diluted with water, extracted with ethyl acetate, dried and concentrated under reduced pressure to give an oil. Yield 0.20 g.

MS: ESI (+ve) 402 (M+1)

ii) N-[4-chloro-2-[2-chloro-4-(2-pyridinyl)phenoxy] phenyl]-glycine

The title compound was prepared by the method of example 5 step v) using the product from step i).

1H NMR DMSO-d6: δ 8.67-8.65 (1H, m), 8.30-8.27 (1H, s), 8.05-7.99 (2H, m), 7.91-7.87 (1H, m), 7.38-7.35 (1H, m), 7.09-6.94 (2H, m), 6.78 (1H, s), 6.67-6.65 (1H, d), 5.75 (1H, bm), 3.87 (2H, s).

MS: ESI (−ve) 386 (M−1)

EXAMPLE 35

4-chloro-2-[2-chloro-4-(ethylsulfonyl)phenoxy]-benzenepropanoic acid

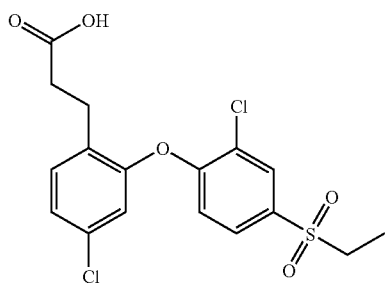

i) 4-chloro-2-hydroxy-benzaldehyde

The subtitle compound was prepared by using 5-chloro-2-hydroxymethylphenol (prepared from the method of Vargha. et. al Acta. Chim. Acad. Hung., 4, 1954, 345-360) (5 g) which was dissolved in DCM (200 ml) and manganese (iv) oxide (10 g) added. The mixture was stirred at room temperature for 16 hours. The mixture was filtered through celite and the filtrate concentrated under reduced pressure to give a brown solid. Yield 3.48 g.

MS: ESI (−ve) 155 (M−1)

ii) 4-chloro-2-hydroxy-benzenepropanoic acid

The subtitle compound was prepared by using the product from step i). (3.48 g) was added to a solution of triethylamine (10 ml) and formic acid (7 ml) in DMF (30 ml) after 20 minutes. Meldrum's acid (3.22 g) was added and the mixture heated to 100 C for 4 hours. The solution was basified with 2M NaOH, extracted with ether (discarded). The aqueous layer was acidified with 2M HCl, extracted with ethyl acetate, dried and concentrated under reduced pressure to give an oil. The residue was purified by chromatography on silica eluting with diethyl ether/isohexane 1:5, yield 0.40 g.

1H NMR CDCl₃: δ 12.07 (1H, s), 9.88 (1H, s), 7.07 (1H, d), 6.80 (1H, s), 6.75 (1H, d), 2.71 (2H, t), 2.45 (2H, t).

iii) 4-chloro-2-[2-chloro-4-(ethylsulfonyl)phenoxy]-benzenepropanoic acid

The title compound was prepared by the method of example 3 step viii) using the product from step ii) and the product from example 4 step i).

1H NMR DMSO-d6: δ 8.06-8.05 (1H, s), 7.80-7.77 (1H, d), 7.47-7.44 (1H, d), 7.28-7.25 (1H, d), 7.14-7.13 (1H, s), 7.01-6.99 (1H, d), 3.53-3.32 (2H, q), 2.68-2.64 (2H, t), 2.16-2.12 (2H, t), 1.30-1.22 (3H, t).

MS: ESI (−ve) 401 (M−1)

EXAMPLE 36

4-chloro-2-[2-cyano-4-(ethylsulfonyl)phenoxy]-benzenepropanoic acid

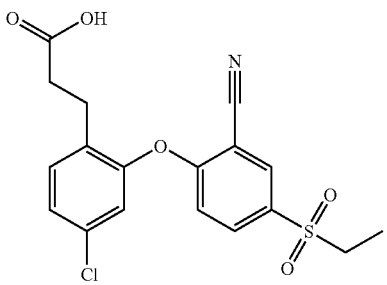

i) 2-chloro-5-(methylthio)-benzonitrile

The subtitle compound was prepared by the method of example 5 step iii) using 2-chloro-5-nitrobenzonitrile. Yield 6.70 g.

1H NMR CDCl₃: δ 7.26-7.24 (1H, d), 6.91-6.90 (1H, m), 6.81-6.77 (1H, d), 3.95-3.80 (2H, bs).

ii) 2-chloro-5-(ethylthio)-benzonitrile

The subtitle compound was prepared by the method of example 5 step iv) using the product from step i) and diethyldisulphide. Yield 2.50 g.

iii) 2-chloro-5-(ethylsulfonyl)-benzonitrile

The subtitle compound was prepared by the method of example 3 step vii) using the product from step ii). Yield 2.10 g.

1H NMR CDCl₃: δ 8.21 (1H, s), 8.06-8.04 (1H, d), 7.76-7.74 (1H, d), 3.18-3.13 (2H, q), 1.34-1.30 (3H, t).

iv) 4-chloro-2-[2-cyano-4-(ethylsulfonyl)phenoxy]-benzenepropanoic acid

The title compound was prepared by the method of example 3 step viii) using the product from step iii) and the product from example 35 step ii).

1H NMR DMSO-d6: δ 8.43 (1H, s), 8.09-8.06 (1H, d), 7.50-7.35 (3H, m), 7.05-7.03 (1H, d), 3.41-3.334 (2H, q), 2.75-2.72 (2H, t), 2.54-2.48 (2H, t), 1.17-1.07 (3H, t).

MS: ESI (−ve) 392 (M−1)

EXAMPLE 37

N-(4-Chloro-2-{2-chloro-4-[(ethylsulfonyl)amino]phenoxy}phenyl)glycine

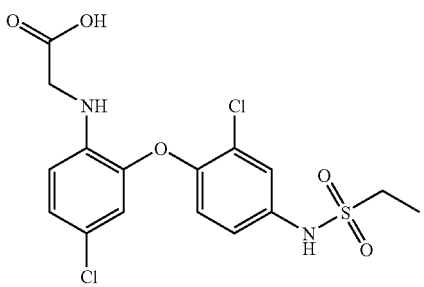

(i) 4-Chloro-2-(2-chloro-4-nitrophenoxy)aniline

A mixture of 2-amino-5-chlorophenol (11.0 g), 2-chloro-1-fluoro-4-nitrobenzene (1.5 g) and potassium carbonate (2.8 g) in dry DMF (20 ml) was stirred room temperature for 1 h then heated at 60° C. for 2 h. The mixture was partitioned between water/ethyl acetate, the organics separated, washed with water, dried and evaporated under reduced pressure. The residue was purified by chromatography on silica eluting with 10% ethylacetate/isohexane, yield 1.96 g.

MS: ESI (+ve) 299/301

(ii) Ethyl N-[4-chloro-2-(2-chloro-4-nitrophenoxy)phenyl]glycinate

A mixture of the product from step (i) (0.3 g), ethyl bromoacetate (0.22 ml) and sodium acetate (0.164 g) in dry ethanol (5 ml) was heated under reflux 7 h. Ethyl bromoacetate (0.5 ml) and sodium acetate (0.34 g) were added and heated for a further 16 h. The solvent was evaporated under reduced pressure and the residue purified by chromatography on silica eluting with 5-7% ethylacetate/isohexane, yield 0.212 g.

$^1$H NMR CDCl$_3$: δ 8.39 (1H, s), 8.07 (1H, d), 7.13 (1H, d), 6.94-6.92 (2H, m), 6.60 (1H, d), 4.63 (1H, brs), 4.22 (2H, q), 3.90 (2H, s), 1.28 (3H, t)

(iii) Ethyl N-[2-(4-amino-2-chlorophenoxy)-4-chlorophenyl]glycinate

A mixture of the product from step (ii) (0.2 g) and Pd(OH)$_2$/C (0.04 g) in ethanol (4 ml) was hydrogenated at 1 Bar for 5 h then filtered. The filtrate was evaporated under reduced pressure and the residue purified by chromatography on silica eluting with 20% ethylacetate/isohexane, yield 0.13 g.

$^1$H NMR CDCl$_3$: δ 6.92-6.88 (2H, m), 6.79 (1H, s), 6.57 (1H, d), 6.51-6.46 (2H, m), 4.25 (2H, q), 3.96 (2H, s), 1.29 (3H, t)

(iv) N-(4-Chloro-2-{2-chloro-4-[(ethylsulfonyl)amino]phenoxy}phenyl)glycine

Ethanesulphonyl chloride (0.1 ml) was added to a mixture of the product from step (iii) (0.11 g) and pyridine (0.5 ml) in DCM (4 ml). After stirring at room temperature for 4 h the mixture was partitioned between diethylether/2 M HCl. The organics separated, dried and evaporated under reduced pressure. The residue was dissolved in methanol (5 ml) then 2M NaOH added and stirred at room temperature for 20 h. The solvent was removed under reduced pressure and the residue partitioned between ethylacetate/1M HCl. The organics were separated, washed with water, dried and evaporated under reduced pressure. The residue was purified by chromatography on silica eluting with 80% ethylacetate/isohexane, yield 0.025 g.

MS: APCI (−ve) 417/9

$^1$H NMR DMSO-d6: δ 9.95 (1H, s), 7.38 (1H, d), 7.18 (1H, dd), 7.05-6.98 (2H, m), 6.62-6.58 (2H, m), 3.89 (2H, s), 3.14 (2H, q), 1.21 (3H, t)

EXAMPLE 38

N-{4-Chloro-2-[3-chloro-4-(trifluoromethyl)phenoxy]phenyl}glycine

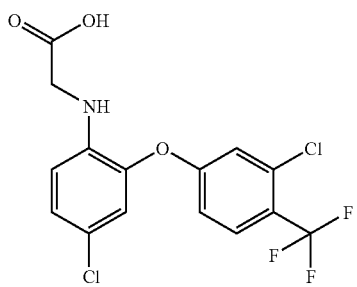

(i) 4-Chloro-2-[3-chloro-4-(trifluoromethyl)phenoxy]aniline

The subtitle compound was prepared by the method of example 37 step (i) using 2-chloro-4-fluorobenzotrifluoride. Yield 0.663 g.

MS: ESI (−ve) 320/322

(ii) Ethyl N-{4-chloro-2-[3-chloro-4-(trifluoromethyl)phenoxy]phenyl}glycinate The subtitle compound was prepared by the method of example 37 step (ii) using the product from step (i). Yield 0.51 g.

MS: ESI (−ve) 406/8

(iii) N-{4-Chloro-2-[3-chloro-4-(trifluoromethyl)phenoxy]phenyl}glycine

A mixture of the product from step (ii) (0.5 g), methanol (5 ml), water (4 ml) and 2M NaOH (2 ml) were stirred at room temperature for 4 h then partitioned between ethylacetate/2 M HCl. The organics were separated, washed with water, dried and evaporated under reduced pressure. The residue was triturated with diethylether/isohexane and filtered, yield 0.1 g.

MS: ESI (−ve) 378/380

$^1$H NMR DMSO-d6: δ 12.62 (1H, s), 7.82 (1H, d), 7.26 (1H, s), 7.17-7.13 (2H, m), 6.99 (1H, d), 6.70 (1H, d), 5.77 (1H, brs), 3.84 (2H, s)

EXAMPLE 39

N-{4-Chloro-2-[4-cyano-2-(trifluoromethyl)phenoxy]phenyl}glycine

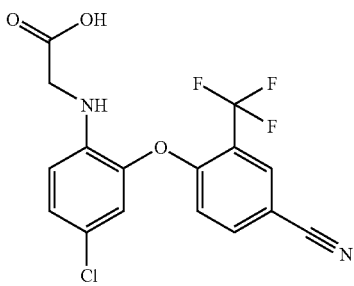

The title compound was prepared by the method of example 38
MS: APCI (−ve) 369
$^1$H NMR DMSO-d6: δ 12.69 (1H, s), 8.35 (1H, s), 8.06 (1H, d), 7.19 (1H, d), 7.07 (1H, s), 6.98 (1H, d), 6.74 (1H, d), 5.53 (1H, s), 3.87 (2H, s)

EXAMPLE 40

N-{4-Chloro-2-[2-cyano-4-(trifluoromethyl)phenoxy]phenyl}glycine

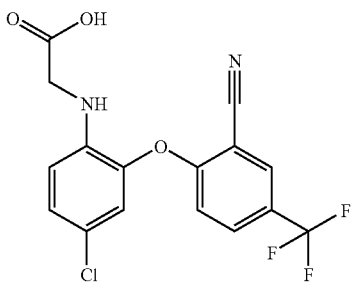

The title compound was prepared by the method of example 38
MS: APCI (−ve) 369
$^1$H NMR DMSO-d6: δ 12.62 (1H, s), 8.40 (1H, s), 7.94 (1H, d), 7.25 (1H, s), 7.20 (1H, d), 6.85 (1H, d), 6.71 (1H, d), 6.00 (1H, brs), 3.84 (2H, s)

EXAMPLE 41

N-{4-Chloro-2-[4-[(methylsulfonyl)amino]-2-(trifluoromethyl)phenoxy]phenyl}glycine

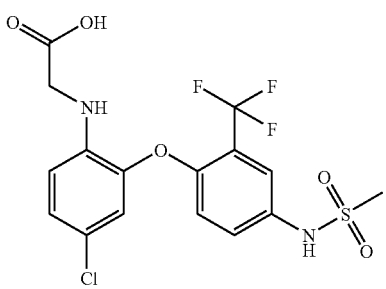

(i) 4-Chloro-2-[4-nitro-2-(trifluoromethyl)phenoxy]aniline

The subtitle compound was prepared by the method of example 37 step (i) using 2-chloro-5-nitrobenzotrifluoride, yield 1.77 g
MS: ESI (−ve) 331/3

(i) Ethyl N-{4-chloro-2-[4-nitro-2-(trifluoromethyl)phenoxy]phenyl}glycinate

The subtitle compound was prepared by the method of example 37 step (ii), yield 1.44 g
MS: ESI (+ve) 419/421

(i) Ethyl N-{4-chloro-2-[4-[(methylsulfonyl)amino]-2-(trifluoromethyl)phenoxy]phenyl}glycinate The product from step (ii) (1.4 g) and PtO$_2$ (0.25 g) in ethylacetate (30 ml) was hydrogenated at 2 Bar for 6 h then filtered. The filtrate was evaporated under reduced pressure and the residue dissolved in DCM (20 ml). Pyridine (5 ml) then methanesulphonyl chloride (1 ml) was added and stirred at room temperature for 4 h. The mixture was partitioned between DCM/2 M HCl. The organics were separated, washed with water, dried and evaporated under reduced pressure. The residue was purified by chromatography on silica eluting with 30% ethylacetate/isohexane, yield 0.64 g.
MS: APCI (−ve) 467/9

(i) N-{4-Chloro-2-[4-[(methylsulfonyl)amino]-2-(trifluoromethyl)phenoxy]phenyl}glycine The title compound was prepared by the method of example 38 step (iii) using the product from step (iii). Yield 0.042 g.
MS: APCI (−ve) 437
$^1$H NMR DMSO-d6: δ 9.94 (1H, s), 7.56 (1H, s), 7.45 (1H, d), 7.08 (1H, d), 7.00 (1H, d), 6.78 (1H, s), 6.67 (1H, d), 5.48 (1H, brs), 3.89 (2H, s), 3.03 (3H, s)

EXAMPLE 42

N-{4-Chloro-2-[4-[methyl(methylsulfonyl)amino]-2-(trifluoromethyl)phenoxy]phenyl}glycine

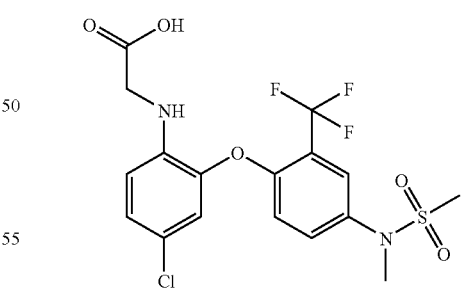

A mixture of the compound from example 41 step (iii) (0.43 g), potassium carbonate (1 g), and methyl iodide (0.4 ml) in DMF (8 ml) was stirred at room temperature for 72 h then partitioned between ethylacetate/water. The organics were separated, washed with water, dried and evaporated under reduced pressure. The residue was dissolved in methanol (8 ml) then 2M NaOH (4 ml) added and stirred at room temperature for 4 h. The solvent was removed under reduced pressure and the residue partitioned between ethylacetate/2

EXAMPLE 43

4-chloro-2-[4-(ethylsulfonyl)-2-(trifluoromethyl)phenoxy]-benzenepropanoic acid

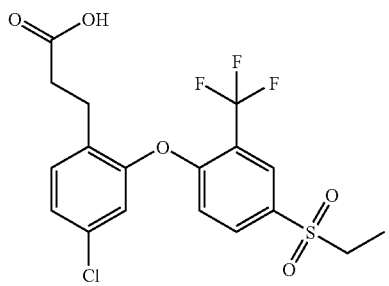

i) 4-(ethylsulfonyl)-1-fluoro-2-(trifluoromethyl)-benzene

The subtitle compound was prepared by the method of example 36 steps ii-iii) using 4-fluoro-3-(1,1,1-trifluoromethyl)aniline. Yield 1.90 g.

1H NMR CDCl$_3$: δ 8.21-8.11 (2H, m), 7.46-7.40 (1H, m), 3.19-3.12 (2H, q), 1.34-1.28 (3H, t).

ii) 4-chloro-2-[4-(ethylsulfonyl)-2-(trifluoromethyl)phenoxy]-benzenepropanoic acid The title compound was prepared by the method of example 3 step viii) using the product from step i) and the product from example 35 step ii).

1H NMR DMSO-d6: δ 8.18 (1H, s), 8.10 (1H, dd), 7.48 (1H, d), 7.36 (1H, dd), 7.31 (1H, s), 7.10 (1H, d), 3.38 (2H, q), 2.89 (2H, t), 2.51 (2H, t), 1.13 (3H, t).

MS: ESI (−ve) 435 (M−1)

EXAMPLE 44

4-chloro-2-[4-(methylsulfonyl)-2-(trifluoromethyl)phenoxy]-benzenepropanoic acid

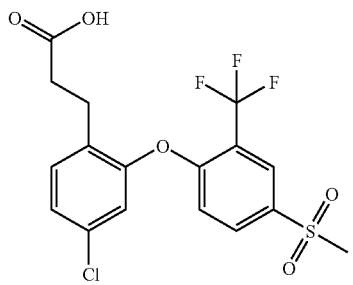

i) 1-fluoro-4-(methylsulfonyl)-2-(trifluoromethyl)-benzene

The subtitle compound was prepared by the method of example 36 steps ii-iii) using 4-fluoro-3-(1,1,1-trifluoromethyl)aniline and dimethyldisulphide. Yield (2.0 g).

1H NMR CDCl$_3$: δ 8.26-8.15 (2H, m), 7.46-7.40 (1H, m), 3.06 (3H, s).

ii) 4-chloro-2-[4-(methylsulfonyl)-2-(trifluoromethyl)phenoxy]-benzenepropanoic acid The title compound was prepared by the method of example 3 step viii) using the product from step i) and the product from example 35 step ii).

1H NMR DMSO-d6: δ 12.17 (1H, s), 8.25 (1H, m), 8.16-8.13 (1H, d), 7.49-7.47 (1H, d), 7.38-7.35 (1H, d), 7.28 (1H, s), 7.11-7.09 (1H, d), 3.30 (3H, s), 2.75-2.67 (2H, t), 2.52-2.47 (2H, t).

MS: ESI (−ve) 421 (M−1)

EXAMPLE 45

4-fluoro-2-[4-(methylsulfonyl)-2-(trifluoromethyl)phenoxy]-benzenepropanoic acid

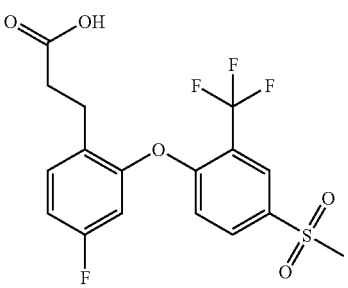

i) 3-(4-fluoro-2-hydroxyphenyl)-(2E)-2-propenoic acid 1,1-dimethylethyl ester The subtitle compound was prepared by using 2-bromo-5-fluorophenol (5.0 g), t-butyl acrylate (3.83 ml), triethylamine (7.25 ml), Palladium(diphenylphosphinoferrocene) dichloride (1.0 g) in dry DMF. The mixture was heated to 100 C for 5 hours. The mixture was diluted with water, extracted with ethyl acetate, dried and concentrated under reduced pressure to give an oil. Yield 2.98 g.

MS: ESI (−ve) 237 (M−1)

ii) 4-fluoro-2-hydroxy-benzenepropanoic acid-1,1-dimethylethyl ester

A mixture of the product from step (i) (2.98 g) and 5% platinum on carbon (0.30 g) in ethyl acetate (30 ml) was hydrogenated at a pressure of 3.50 bar overnight. The mixture was filtered through celite and the filtrate concentrated under reduced pressure to give an oil (1.17 g).

1H NMR CDCl$_3$: δ 8.05 (1H, s), 7.26-7.13 (1H, m), 7.01-6.96 (1H, m), 3.06 (1H, s), 2.81-2.77 (2H, t), 2.63-2.59 (2H, t), 1.42 (9H, s).

---

M HCl. The organics were separated, washed with water, dried and evaporated under reduced pressure. The residue was purified by RPHPLC yield 0.092 g.

MS: APCI (−ve) 451

$^1$H NMR CDCl$_3$: δ 12.70 (1H, s), 7.76 (1H, s), 7.64 (1H, d), 7.13 (1H, d), 6.95 (1H, d), 6.90 (1H, s), 6.71 (1H, d), 5.51 (1H, s), 3.89 (2H, s), 3.26 (3H, s), 2.99 (3H, s)

iii) 4-fluoro-2-[4-(methylsulfonyl)-2-(trifluoromethyl)phenoxy]-benzenepropanoic acid The title compound was prepared by the method of example 3 step viii) using the product from step ii) and the product from example 44 step i).

1H NMR DMSO-d6: δ 12.15 (1H, s), 8.25 (1H, s), 8.16-8.13 (1H, d), 7.51-7.47 (1H, m), 7.18-7.09 (3H, m), 3.28 (3H, s), 2.74-2.67 (2H, t), 2.52-2.45 (2H, t).

MS: ESI (−ve) 405 (M−1)

EXAMPLE 46

2-[4-(ethylsulfonyl)-2-(trifluoromethyl)phenoxy]-4-fluoro-benzenepropanoic acid

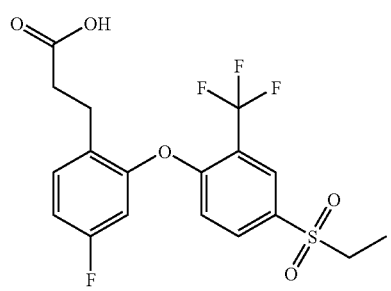

The title compound was prepared by the method of example 45 using the product from example 43 step i).

1H NMR DMSO-d6: δ 8.19-8.18 (1H, s), 8.12-8.09 (1H, d), 7.51-7.48 (1H, t), 7.18-7.11 (3H, m), 3.42-3.37 (2H, q), 2.74-2.70 (2H, t), 2.51-2.45 (2H, t), 1.17-1.11 (3H, s).

MS: ESI (−ve) 419 (M−1)

EXAMPLE 47

2-[2-cyano-4-(ethylsulfonyl)phenoxy]-4-fluoro-benzenepropanoic acid

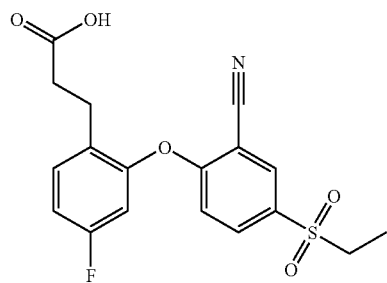

The title compound was prepared by the method of example 45 using the product from example 36 step i).

1H NMR DMSO-d6: δ 8.44-8.43 (1H, s), 8.09-8.06 (1H, d), 7.52-7.48 (1H, t), 7.26-7.15 (2H, m), 7.07-7.05 (1H, d), 3.41-3.34 (2H, q), 2.75-2.71 (2H, t), 2.52-2.47 (2H, t), 1.14-1.07 (3H, s).

MS: ESI (−ve) 376 (M−1)

EXAMPLE 48

2-[2-cyano-4-(methylsulfonyl)phenoxy]-4-fluoro-benzenepropanoic acid

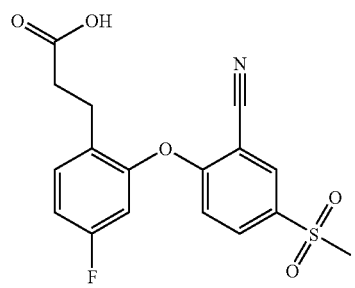

i) 2-chloro-5-(methylsulfonyl)-benzonitrile

The subtitle compound was prepared using the method of example 36 steps i-iii) using dimethyldisulphide. Yield 2.0 g 1H NMR CDCl₃: δ 8.26 (1H, s), 8.11-8.08 (1H, d), 7.77-0.775 (1H, d), 3.10 (3H, s).

ii) 2-[2-cyano-4-(methylsulfonyl)phenoxy]-4-fluoro-benzenepropanoic acid

The title compound was prepared by the method of example 45 using the product from step i).

1H NMR DMSO-d6: δ 8.49 (1H, s), 8.13-8.10 (1H, d), 7.52-7.47 (1H, t), 7.23-7.14 (2H, m), 7.04-7.01 (1H, d), 3.28 (3H, s), 2.72-2.67 (2H, t), 2.42-2.37 (2H, t).

MS: ESI (−ve) 362 (M−1)

EXAMPLE 49

4-chloro-2-[[2-chloro-4-(methylsulfonyl)phenyl]amino]-benzenepropanoic acid

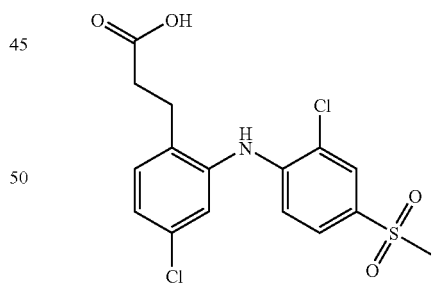

i) 3-(4-chloro-2-nitrophenyl)-(2E)-2-propenoic acid ethyl ester 1-bromo-4-chloro-2-nitrobenzene (5 g), triethylamine (4.42 ml), ethyl acrylate (22.9 ml), palladium (II) acetate (0.048 g) and triphenylphosphine (0.111 g) in DMF (30 ml) was refluxed at 87° C. for 10 h. Toluene was added and the mixture washed with 2M hydrochloric acid and water. The organics were dried and concentrated under reduced pressure to a brown oil which was triturated with isohexane to give a light brown solid. Yield 4.95 g.

1H NMR CDCl3: δ 8.07-8.02 (2H, m), 7.68-7.47 (2H, m), 6.39-6.33 (1H, d), 4.33-4.26 (2H, q) 1.37-1.32 (3H, t)

ii) 7-chloro-3,4-dihydro-2(1H)-quinolinone

A mixture of the product from step (i) (4.95 g) and 5% platinum on carbon (0.400 g) and a few drops of 2M hydrochloric acid in ethyl acetate (30 ml) was hydrogenated under a pressure of 3 bar. The catalyst was removed by filtration through celite and the filtrate was evaporated under reduced pressure to a brown solid, which was triturated with diethyl ether to give a pink solid. Yield 1.28 g 1H NMR DMSO-d6: δ 10.17 (1H, s), 7.20-7.18 (1H, d), 6.96-6.93 (1H, d), 6.87 (1H, s), 2.87-2.84 (2H, t), 2.47-2.44 (2H, t)

iii) 4-chloro-2-[[2-chloro-4-(methylsulfonyl)phenyl]amino]-benzenepropanoic acid A solution of the product from step (ii) (0.174 g) and sodium hydride (60% wt. disp. oil, 0.039 g) in DMF (10 ml) was stirred at 50° C. for 1 hour. The product from example 3 step (vi)-(vii) (0.200 g) was added and the mixture was refluxed at 90° C. for 3 hours. The mixture was partitioned between 2M sodium hydroxide and diethyl ether. The aqueous layer was acidified with 2M hydrochloric acid, extracted with ethyl acetate and the organic layer dried and concentrated under reduced pressure to give an oil. The residue was purified using RP prep HPLC. Yield 0.061 g 1H NMR DMSO-d6: δ 8.34 (1H, s), 7.86 (1H, s), 7.62-7.59 (1H, d), 7.42-7.40 (1H, d), 7.32-7.27 (2H, m), 6.64-6.62 (1H, d), 3.17 (3H, s), 2.74-2.69 (2H, t), 2.54-2.50 (2H, t)

MS: ESI (−ve) 386 (M−1)

EXAMPLE 50

4-chloro-2-[[2-chloro-4-(ethylsulfonyl)phenyl]amino]-benzenepropanoic acid

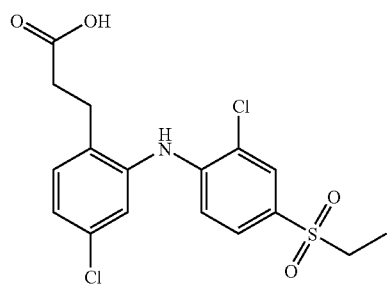

A solution of the product from example 49 step (iii) (0.163 g) and the product of example 4 step (i) (0.200 g) and caesium carbonate (0.239 g) in NMP (10 ml) was refluxed at 100° C. for 3 hours. The mixture was partitioned between 2M sodium hydroxide and diethyl ether. The aqueous layer was acidified with 2M hydrochloric acid, extracted with ethyl acetate and the organic layer dried and concentrated under reduced pressure to give an oil. The residue was purified using RP prep HPLC. Yield 0.044 g.

1H NMR DMSO-d6: δ 8.40 (1H, s), 7.79 (1H, s), 7.58-7.54 (1H, d), 7.42-7.39 (1H, d), 7.32-7.29 (2H, m), 6.65-6.62 (1H, d), 3.31-3.20 (4H, m), 2.73-2.69 (2H, t), 1.21-1.07 (3H, q)

MS: ESI (−ve) 400 (M−1)

EXAMPLE 51

4-chloro-2-[[2-chloro-4-(methylsulfonyl)phenyl]amino]-benzenepropanoic acid

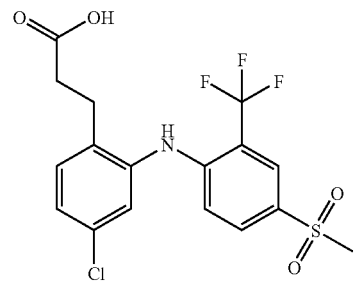

The title compound was prepared using the method of example 49 using the product from example 44 step i).

1H NMR DMSO-d6: δ 12.40 (1H, s), 8.28 (1H, s), 7.97 (1H, m), 7.84-7.82 (1H, d), 7.45-7.31 (3H, m), 6.64-6.62 (1H, d), 3.18 (3H, s), 2.70-2.67 (2H, t), 2.54-2.50 (2H, t)

MS: ESI (−ve) 420 (M−1)

EXAMPLE 52

4-chloro-2-[[2-chloro-4-(ethylsulfonyl)phenyl]amino]-benzenepropanoic acid

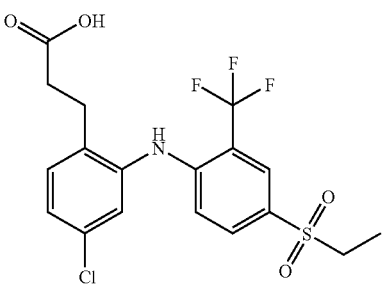

The title compound was prepared using the method of example 49 using the product from example 43 step i).

1H NMR DMSO-d6: δ 8.54 (1H, bs), 7.90 (1H, s), 7.79-7.77 (1H, d), 7.44-7.32 (3H, m), 6.67-6.65 (1H, d), 3.28-3.22 (2H, q), 2.68-2.65 (2H, t), 2.51-2.47 (2H, t), 1.11-1.08 (3H, t).

MS: ESI (−ve) 434 (M−1)

EXAMPLE 53

4-chloro-2-[4-(methylsulfonyl)-2-(trifluoromethyl)phenoxy]-benzeneacetic acid

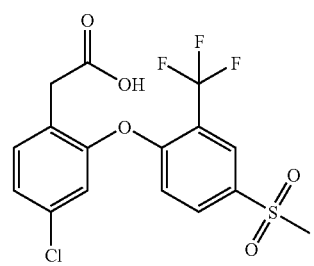

i) 4-chloro-2-methoxy-benzeneacetic acid

A solution of 4-chloro-2-methoxy-benzyl alcohol (4 g) and thionyl chloride (10 ml) in dichloromethane (30 ml) was refluxed for 1 h. The solution was concentrated under reduced pressure and the residue partitioned between diethyl ether and water. The organics were dried and evaporated under reduced pressure. This residue and sodium cyanide (1 g) in DMF (20 ml) was stirred at room temperature for 3 h. The mixture was partitioned between diethyl ether and water, the organics were dried and evaporated under reduced pressure. A solution of potassium hydroxide was added to the residue and the mixture heated under reflux for 24 h. The mixture was partitioned between diethyl ether and water, the aqueous layer was acidified with 2M hydrochloric acid and extracted with ethyl acetate. The organic layer was dried and evaporated under reduced pressure. The residue was triturated with diethyl ether and isohexane. Yield 1.4 g.

$^1$H NMR CDCl$_3$: δ 7.11 (1H, d), 6.92 (1H, d), 6.87 (1H, s), 3.82 (3H, s), 3.62 (2H, s)

ii) 4-chloro-2-hydroxy-benzeneacetic acid 4-chloro-2-methoxy-benzeneacetic acid (1.4 g), HBr (25 ml), acetic acid (5 ml) were refluxed for 48 h then evaporated under reduced pressure. The residue was azeotroped with toluene and triturated with diethyl ether and isohexane. Yield 0.56 g.

1H NMR CDCl$_3$: δ 7.12 (1H, d), 6.81-6.76 (2H, m), 3.45 (2H, s)

iii) 4-chloro-2-[4-(methylsulfonyl)-2-(trifluoromethyl)phenoxy]-benzeneacetic acid A solution of the product from step (ii) (0.125 g), the product of example 44 step (i) (0.150 g) and cesium carbonate (0.437 g) in NMP (10 ml) was stirred at 80° C. for 10 h. The mixture was partitioned between 2M sodium hydroxide and diethyl ether. The aqueous layer was acidified with 2M hydrochloric acid, extracted with ethyl acetate and the organic layer dried and evaporated under reduced pressure. The residue was purified using RP prep HPLC. Yield 0.025 g.

1H NMR DMSO-d6: δ 12.39 (1H, br.s), 8.23 (1H, s), 8.16-8.14 (1H, d), 7.52-7.50 (1H, d), 7.39-7.37 (1H, d), 7.31 (1H, s), 7.14-7.12 (1H, d), 3.58 (2H, s), 3.30 (3H, s)
MS: ESI (−ve) 407 (M−1)

EXAMPLE 54

4-chloro-2-[[4-(methylsulfonyl)-2-(trifluoromethyl)phenyl]thio]-benzene propanoic acid

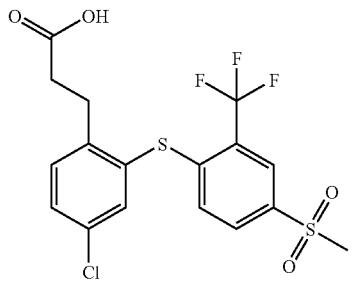

i) 4-chloro-2-(methylthio)-benzaldehyde

The subtitle compound was prepared by using 2-chloro-4-fluorobenzaldehyde (1.16 g) in dry DMF (20 ml). The mixture was treated with sodium thiomethoxide (0.52 g) and heated to 50° C. for 2 hours. The mixture was diluted with water, extracted with ethyl acetate, dried and concentrated under reduced pressure to give a solid. The residue was purified by chromatography on silica eluting with isohexane/diethylether 2:1 to give a white solid, yield 0.70 g.

1H NMR CDCl$_3$: δ 10.19 (1H, s), 7.74-7.72 (1H, d), 7.28-7.23 (2H, m), 2.50-2.49 (3H, s).

ii) 3-[4-chloro-2-(methylthio)phenyl]-(2E)-2-propenoic acid ethyl ester

The subtitle compound was prepared from the method of example 3 step iv) using the product from step i). Yield 0.95 g.

MS: ESI (+ve) 257 (M+1)

iii) 4-chloro-2-mercapto-benzenepropanoic acid

The subtitle compound was prepared by using the product from step ii) (0.7 g) which was dissolved in DCM (30 ml) and cooled to 0° C. before adding 70% m-CPBA (0.46 g). The mixture was kept at 0 C for 2 hours, washed with a solution of sodium hydrogen carbonate, dried and concentrated under reduced pressure to an oil. The oil was dissolved in DCM (10 ml) and cooled to 0° C. before adding trifluoroacetic anhydride (0.40 ml). The mixture was stirred at room temperature overnight. The mixture was concentrated under reduced pressure to an oil and dissolved in ethanol (10 ml). Triethylamine (10 ml) was added and the mixture stirred at room temperature for 1 hour. The mixture was concentrated under reduced pressure to an oil which was dissolved in diethyl ether, washed with aqueous sodium hydroxide. The aqueous layer was acidified with 2M HCl, extracted with ethyl acetate, dried and concentrated under reduced pressure to give a white solid. Yield 0.26 g.

1H NMR DMSO-d6: δ 7.35-7.11 (3H, m), 5.69 (1H, s), 2.80-2.74 (2H, t), 2.54-2.50 (2H, t).
MS: ESI (−ve) 215 (M−1)

iv) 4-chloro-2-[[4-(methylsulfonyl)-2-(trifluoromethyl)phenyl]thio]-benzenepropanoic acid Sodium hydride (60% wt. disp. oil, 0.063 g) was added to a solution of the product from step (iii) (0.180 g) in dry DMF (10 ml) and stirred at RT for 1 h before adding the product from example 44 step (i) (0.188 g). The mixture was heated at 80° C. for 1 h, then partitioned between 2M hydrochloric acid/ethyl acetate. The organics were dried, concentrated under reduced pressure to give an oil. The residue was purified by reverse phase HPLC.

1H NMR DMSO-d6: δ 8.20-8.19 (1H, s), 8.03-8.00 (1H, d), 7.63-7.54 (3H, m), 7.08-7.05 (1H, d), 3.16 (3H, s), 2.90-2.86 (2H, t), 2.49-2.47 (2H, t).
MS: ESI (−ve) 437 (M−1)

EXAMPLE 55

4-chloro-2-[2-fluoro-4-(methylsulfonyl)phenoxy]-benzenepropanoic acid

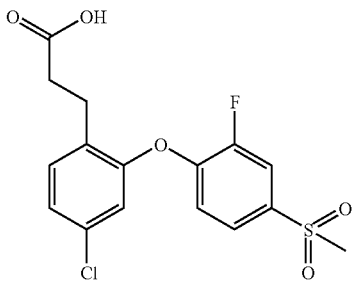

The title compound was prepared by the method of example 35 step iii) using 3,4-difluorophenylmethylsulphone and the product of example 35 step ii).

1H NMR DMSO-d6: δ 8.00-7.97 (1H, d), 7.75-7.72 (1H, d), 7.44-7.42 (1H, d), 7.29-7.26 (1H, d), 7.19-7.12 (2H, m), 3.26 (3H, s), 2.80-2.69 (2H, t), 2.50-2.45 (2H, t).

MS: ESI (−ve) 371 (M−1)

EXAMPLE 56

4-chloro-2-[2-chloro-4-(methylsulfonyl)phenoxy]-benzenepropanoic acid

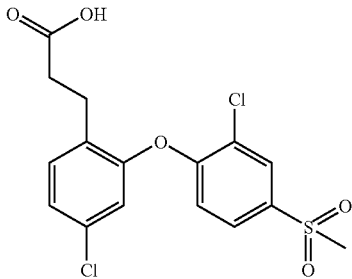

The title compound was prepared by the method of example 35 step iii) using the products from example 3 step vii) and example 35 step ii).

1H NMR DMSO-d6: δ 8.14 (1H, s), 7.86-7.83 (1H, d), 7.46-7.44 (1H, d), 7.32-7.29 (1H, d), 7.13-7.07 (2H, m), 3.33-3.27 (5H, m), 2.75-2.73 (2H, t).

MS: ESI (−ve) 386 (M−1)

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well). Compounds of formula (I) have an IC$_{50}$ value of less than (<) 10 μM.

Specifically, example 5 has a pIC$_{50}$=8.6, example 7 has a pIC$_{50}$=9.1 and example 37 has a pIC$_{50}$=8.6.

The invention claimed is:

1. A compound of formula (I) or a pharmaceutically acceptable salt thereof:

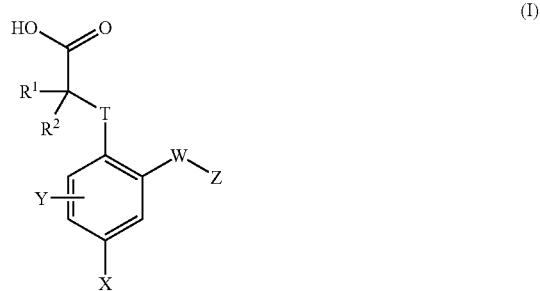

(I)

in which:

T is CR$^1$R$^2$;

W is O;

X is trifluoromethyl or halogen;

Y is selected from hydrogen, halogen, CN, nitro, SO$_2$R$^3$, OR$^4$, SR$^4$, SOR$^3$, SO$_2$NR$^4$R$^5$, CONR$^4$R$^5$, NR$^4$R$^5$, NR$^6$SO$_2$R$^3$, NR$^6$CO$_2$R$^5$, NR$^6$COR$^3$, C$_2$-C$_6$ alkenyl, C$_2$-C$_6$ alkynyl, C$_3$-C$_7$ cycloalkyl or C$_{1-6}$alkyl, the latter four groups being optionally substituted by one or more substituents independently selected from halogen, $OR^6$ and $NR^6R^7$, $S(O)_nR^6$ where n is 0, 1 or 2;

Z is aryl or heteroaryl, optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, $NR^6CONR^4R^5$, $NR^6SO_2NR^4R^5$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$ $R^1$ and $R^2$ independently represent a hydrogen atom, halogen, $C_2$-$C_6$ alkenyl, $C_2$-$C_6$ alkynyl, $C_3$-$C_7$ cycloalkyl or a $C_{1-6}$alkyl group, the latter four groups being optionally substituted by one or more substituents independently selected from halogen, $C_3$-$C_7$ cycloalkyl, $NR^6R^7$, $OR^6$, $S(O)_nR^6$ (where n is 0, 1 or 2);

or $R^1$ and $R^2$ together can form a 3-8 membered ring optionally containing one or more atoms selected from O, S, $NR^6$ and itself optionally substituted by one or more $C_1$-$C_3$ alkyl or halogen;

$R^3$ represents $C_3$-$C_7$ cycloalkyl, $C_{1-6}$alkyl, $C_2$-$C_6$ alkenyl or $C_2$-$C_6$ alkynyl all of which may be optionally substituted by one or more substituents independently selected from halogen, $C_3$-$C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

$R^4$ and $R^5$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^4$ and $R^5$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_{1-3}$ alkyl;

$R^6$ and $R^7$ independently represents a hydrogen atom or $C_1$-$C_6$ alkyl;

$R^8$ is hydrogen, $C_{1-4}$ alkyl, —$COC_1$-$C_4$ alkyl, $CO_2C_1$-$C_4$alkyl or $CONR^6C_1$-$C_4$alkyl;

$R^9$ represents aryl, heteroaryl, $C_3$-$C_7$ cycloalkyl or $C_{1-6}$alkyl, the latter two groups may be optionally substituted by one or more substituents independently selected from halogen, $C_3$-$C_7$ cycloalkyl, aryl, heteroaryl $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

$R^{10}$ and $R^{11}$ independently represent aryl or heteroaryl, hydrogen, $C_3$-$C_7$ cycloalkyl or $C_{1-6}$alkyl, the latter two groups being optionally substituted by one or more substituents independently selected from halogen, $C_3$-$C_7$ cycloalkyl, aryl, heteroaryl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^{10}$ and $R^{11}$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_1$-$C_3$ alkyl, and $R^{12}$ represents a hydrogen atom or $C_{1-6}$alkyl which may be substituted by one or more halogen atoms, provided that the substituent on group Z cannot be $NR^{10}R^{11}$, where $R^{10}R^{11}$ are independently hydrogen, aryl, or alkyl.

2. A compound according to claim 1 in which Y is hydrogen or $C_{1-6}$alkyl.

3. A compound according to claim 1 in which Z is phenyl, optionally substituted.

4. A compound according to claim 1 in which $R^1$ and $R^2$ are independently hydrogen or $C_{1-3}$ alkyl.

5. A compound according to claim 1 selected from:
3-[2-(3-Cyanophenoxy)-4-(trifluoromethyl)phenyl]propanoic acid;
3-[2-[2-Chloro-4-(methylsulfonyl)phenoxy]-4-(trifluoromethyl)phenyl]propanoic acid;
3-[2-[2-Chloro-4-(ethylsulfonyl)phenoxy]-4-(trifluoromethyl)phenyl]propanoic acid;
3-{2-[2-Chloro-4-(methylsulfonyl)phenoxy]-4-fluorophenyl}propanoic acid;
{2-[2-Chloro-4-(methylsulfonyl)phenoxy]-4-fluorophenyl}acetic acid;
4-chloro-2-[2-chloro-4-(methylsulfonyl)phenoxy]-α-methyl-benzenepropanoic acid;
2-[2-chloro-4-(ethylsulfonyl)phenoxy]-4-fluoro-benzenepropanoic acid;
2-[4-(ethylsulfonyl)-3-(trifluoromethyl)phenoxy]-4-fluoro-benzenepropanoic acid;
4-chloro-2-[2-chloro-4-(ethylsulfonyl)phenoxy]-benzenepropanoic acid;
4-chloro-2-[2-cyano-4-(ethylsulfonyl)phenoxy]-benzenepropanoic acid;
4-chloro-2-[4-(ethylsulfonyl)-2-(trifluoromethyl)phenoxy]-benzenepropanoic acid;
4-chloro-2-[4-(methylsulfonyl)-2-(trifluoromethyl)phenoxy]-benzenepropanoic acid;
4-fluoro-2-[4-(methylsulfonyl)-2-(trifluoromethyl)phenoxy]-benzenepropanoic acid;
2-[4-(ethylsulfonyl)-2-(trifluoromethyl)phenoxy]-4-fluoro-benzenepropanoic acid;
2-[2-cyano-4-(ethylsulfonyl)phenoxy]-4-fluoro-benzenepropanoic acid;
2-[2-cyano-4-(methylsulfonyl)phenoxy]-4-fluoro-benzenepropanoic acid;
4-chloro-2-[[2-chloro-4-(methylsulfonyl)phenyl]amino]-benzenepropanoic acid;
4-chloro-2-[[2-chloro-4-(ethylsulfonyl)phenyl]amino]-benzenepropanoic acid;
4-chloro-2-[[2-chloro-4-(methylsulfonyl)phenyl]amino]-benzenepropanoic acid;
4-chloro-2-[[2-chloro-4-(ethylsulfonyl)phenyl]amino]-benzenepropanoic acid;
4-chloro-2-[2-fluoro-4-(methylsulfonyl)phenoxy]-benzenepropanoic acid, and
4-chloro-2-[2-chloro-4-(methylsulfonyl)phenoxy]-benzenepropanoic acid,
and pharmaceutically acceptable salts thereof.

6. A method of treating asthma or rhinitis, which comprises administering to a patient a therapeutically effective amount of a compound of formula (I) or a pharmaceutically acceptable salt as defined in claim 1.

* * * * *

UNITED STATES PATENT AND TRADEMARK OFFICE
CERTIFICATE OF CORRECTION

PATENT NO. : 8,022,248 B2  
APPLICATION NO. : 11/571707  
DATED : September 20, 2011  
INVENTOR(S) : Roger Victor Bonnert et al.

Page 1 of 1

It is certified that error appears in the above-identified patent and that said Letters Patent is hereby corrected as shown below:

Column 62, line 65, "$NR^6CO_2R^5$" should read -- $NR^6CO_2R^6$ --

Column 63, line 15, "$NR^6SO_2R^7$" should read -- $NR^6SO_2R^7$; --.

Column 63, lines 44-45 and Column 64, line 1, each occurrence of "heterocylic" should read -- heterocyclic --.

Column 63, lines 54-55, "heteroaryl" should read -- heteroaryl, --.

Column 64, line 53, cancel the text beginning with "4-chloro-2-[[2-chloro-4-(methylsulfonyl)phenyl]amino]-" to and ending with "benzenepropanoic acid;" in column 64, line 56.

Column 64, line 64, "(I)" should read -- (I), --.

Signed and Sealed this  
Eighth Day of November, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 8,022,248 B2 | Page 1 of 1 |
| APPLICATION NO. | : 11/571707 | |
| DATED | : September 20, 2011 | |
| INVENTOR(S) | : Roger Victor Bonnert | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this
Twenty-first Day of February, 2012

David J. Kappos
*Director of the United States Patent and Trademark Office*